United States Patent
Du et al.

(10) Patent No.: US 12,290,264 B2
(45) Date of Patent: May 6, 2025

(54) DUAL ULTRASONIC CATHETER AND METHODS OF USE

(71) Applicant: Ultratellege USA Co., Limited, Erie, PA (US)

(72) Inventors: Shu Du, Erie, PA (US); Tao Song, Erie, PA (US)

(73) Assignee: Ultratellege USA Co., Limited, Erie, PA (US)

( * ) Notice: Subject to any disclaimer, the term of this patent is extended or adjusted under 35 U.S.C. 154(b) by 686 days.

(21) Appl. No.: 17/471,419

(22) Filed: Sep. 10, 2021

(65) Prior Publication Data

US 2022/0233199 A1 Jul. 28, 2022

Related U.S. Application Data

(60) Provisional application No. 63/140,372, filed on Jan. 22, 2021.

(51) Int. Cl.
*A61B 17/22* (2006.01)
*A61B 17/00* (2006.01)
*A61B 17/12* (2006.01)

(52) U.S. Cl.
CPC .. *A61B 17/12109* (2013.01); *A61B 17/12031* (2013.01); *A61B 17/22012* (2013.01); *A61B 2017/12095* (2013.01)

(58) Field of Classification Search
CPC .. A61B 17/12109; A61B 17/12022–17/12195;
(Continued)

(56) References Cited

U.S. PATENT DOCUMENTS

| | | |
|---|---|---|
| 3,325,781 A | 6/1967 | Harris |
| 3,433,226 A | 3/1969 | Boyd |

(Continued)

FOREIGN PATENT DOCUMENTS

| | | |
|---|---|---|
| EP | 0634189 A2 | 1/1995 |
| EP | 1380265 A1 | 1/2004 |

(Continued)

OTHER PUBLICATIONS

International Search Report and Written Opinion for PCT Application No. PCT/US2021/049791, mailed Nov. 30, 2021.

(Continued)

*Primary Examiner* — Kathleen S Holwerda
*Assistant Examiner* — Daniel Icet
(74) *Attorney, Agent, or Firm* — Mills IP Law, PLLC

(57) ABSTRACT

An apparatus includes a transducer assembly including a transducer housing and an ultrasonic transducer disposed within the transducer housing. A transducer horn is disposed at least partially within the transducer housing and includes a probe coupling. A first probe includes a first coupler and a first elongate member coupled to the first coupler. The first coupler has a first coupling portion and a second coupling portion, and the first coupling portion is configured to be releasably coupled to the probe coupling of the transducer horn such that the first probe is coupled to the ultrasonic transducer. A second probe includes a second coupler and a second elongate member coupled to the second coupler. The second coupler has a third coupling portion releasably couplable to the second coupling portion of the first coupler such that the second probe is coupled to the ultrasonic transducer.

10 Claims, 23 Drawing Sheets

DETAIL B

(58) Field of Classification Search
CPC .................. A61B 17/22–2017/22098; A61B 17/320068–2017/320098; A61N 7/00; A61N 2007/0078
See application file for complete search history.

(56) References Cited

U.S. PATENT DOCUMENTS

| | | |
|---|---|---|
| 3,872,472 A | 3/1975 | Moschgat |
| 3,893,106 A | 7/1975 | Schulein |
| 4,165,649 A | 8/1979 | Greer |
| 4,169,984 A | 10/1979 | Parisi |
| 4,397,186 A | 8/1983 | Phelan et al. |
| 4,474,180 A | 10/1984 | Angulo |
| 4,660,573 A | 4/1987 | Brumbach |
| 4,802,458 A | 2/1989 | Finsterwald et al. |
| 4,886,491 A | 12/1989 | Parisi et al. |
| 4,893,628 A | 1/1990 | Angelsen |
| 4,920,954 A | 5/1990 | Alliger et al. |
| 4,933,918 A | 6/1990 | Landsrath et al. |
| 5,358,505 A | 10/1994 | Wuchinich |
| 5,388,584 A * | 2/1995 | King ............... A61B 8/4488 174/113 R |
| 5,391,144 A * | 2/1995 | Sakurai ............ A61B 18/1402 601/3 |
| 5,397,301 A | 3/1995 | Pflueger et al. |
| 5,427,118 A | 6/1995 | Nita et al. |
| 5,447,509 A | 9/1995 | Mills et al. |
| 5,527,273 A | 6/1996 | Manna et al. |
| 5,540,656 A | 7/1996 | Pflueger et al. |
| 5,562,609 A | 10/1996 | Brumbach |
| 5,630,837 A | 5/1997 | Crowley |
| 5,674,235 A | 10/1997 | Parisi |
| 5,680,865 A | 10/1997 | Tanaka |
| 5,720,710 A | 2/1998 | Tachibana et al. |
| 5,735,280 A | 4/1998 | Sherman et al. |
| 5,746,756 A | 5/1998 | Bromfield et al. |
| 5,827,201 A | 10/1998 | Samson et al. |
| 5,897,569 A | 4/1999 | Kellogg et al. |
| 5,906,628 A | 5/1999 | Miyawaki et al. |
| 5,989,275 A | 11/1999 | Estabrook et al. |
| 6,050,971 A | 4/2000 | Garnier |
| 6,063,098 A | 5/2000 | Houser et al. |
| 6,071,260 A | 6/2000 | Halverson |
| 6,093,150 A | 7/2000 | Chandler et al. |
| 6,165,163 A | 12/2000 | Chien et al. |
| 6,217,543 B1 | 4/2001 | Anis et al. |
| 6,274,963 B1 | 8/2001 | Estabrook et al. |
| 6,296,620 B1 | 10/2001 | Gesswein et al. |
| 6,299,591 B1 | 10/2001 | Banko |
| 6,383,183 B1 | 5/2002 | Sekino et al. |
| 6,450,975 B1 | 9/2002 | Brennan et al. |
| 6,503,205 B2 | 1/2003 | Manor et al. |
| 6,508,781 B1 | 1/2003 | Brennan et al. |
| 6,511,478 B1 | 1/2003 | Burnside et al. |
| 6,514,220 B2 | 2/2003 | Melton, Jr. et al. |
| 6,524,299 B1 | 2/2003 | Tran et al. |
| 6,577,042 B2 | 6/2003 | Lee et al. |
| 6,623,444 B2 | 9/2003 | Babaev |
| 6,689,086 B1 | 2/2004 | Nita et al. |
| 6,743,239 B1 | 6/2004 | Kuehn et al. |
| 6,819,027 B2 | 11/2004 | Saraf |
| 6,866,670 B2 | 3/2005 | Rabiner et al. |
| 6,875,220 B2 | 4/2005 | Du et al. |
| 6,942,677 B2 | 9/2005 | Nita et al. |
| 7,089,063 B2 | 8/2006 | Lesh et al. |
| 7,204,820 B2 | 4/2007 | Akahoshi |
| 7,214,191 B2 | 5/2007 | Stringer et al. |
| 7,229,455 B2 * | 6/2007 | Sakurai ......... A61B 17/320092 606/128 |
| 7,335,169 B2 | 2/2008 | Thompson et al. |
| 7,335,180 B2 | 2/2008 | Nita et al. |
| 7,371,235 B2 | 5/2008 | Thompson et al. |
| 7,431,728 B2 | 10/2008 | Gerry et al. |
| 7,494,467 B2 | 2/2009 | Makin et al. |
| 7,494,468 B2 | 2/2009 | Rabiner et al. |
| 7,503,895 B2 | 3/2009 | Rabiner et al. |
| 7,682,366 B2 | 3/2010 | Sakurai et al. |
| 7,806,828 B2 | 10/2010 | Stringer |
| 7,819,810 B2 | 10/2010 | Stringer et al. |
| 7,918,852 B2 | 4/2011 | Tullis et al. |
| 7,955,293 B2 | 6/2011 | Nita et al. |
| 8,052,607 B2 | 11/2011 | Byrd |
| 8,062,566 B2 | 11/2011 | Nita et al. |
| 8,115,366 B2 | 2/2012 | Hoffman et al. |
| 8,133,236 B2 | 3/2012 | Nita |
| 8,152,753 B2 | 4/2012 | Nita et al. |
| 8,182,467 B2 | 5/2012 | Nguyen et al. |
| 8,221,343 B2 | 7/2012 | Nita et al. |
| 8,246,643 B2 | 8/2012 | Nita |
| 8,308,677 B2 | 11/2012 | Nita et al. |
| 8,454,639 B2 | 6/2013 | Du et al. |
| 8,585,724 B2 | 11/2013 | Palmer |
| 8,721,581 B2 | 5/2014 | Zolli |
| 8,845,541 B2 | 9/2014 | Strunk et al. |
| 9,615,844 B2 | 4/2017 | Du et al. |
| 9,713,481 B2 | 7/2017 | Du et al. |
| 9,763,684 B2 | 9/2017 | Du et al. |
| 9,931,161 B2 | 4/2018 | Willis |
| 10,052,120 B2 | 8/2018 | Du et al. |
| 10,231,712 B2 | 3/2019 | Ebbini et al. |
| 10,314,648 B2 | 6/2019 | Ge et al. |
| 10,368,897 B2 | 8/2019 | Uhlrich et al. |
| 10,582,983 B2 | 3/2020 | Roll Hoye |
| 10,702,337 B2 | 7/2020 | Waldstreicher et al. |
| 2002/0055754 A1 | 5/2002 | Ranucci et al. |
| 2002/0077550 A1 | 6/2002 | Rabiner et al. |
| 2002/0077643 A1 | 6/2002 | Rabiner et al. |
| 2003/0036705 A1 | 2/2003 | Hare et al. |
| 2003/0212333 A1 | 11/2003 | Rabiner et al. |
| 2004/0127925 A1 | 7/2004 | Du et al. |
| 2005/0085748 A1 | 4/2005 | Culp et al. |
| 2005/0209620 A1* | 9/2005 | Du ............. A61B 17/32053 606/167 |
| 2006/0004396 A1 | 1/2006 | Easley et al. |
| 2006/0090956 A1 | 5/2006 | Peshknvsky et al. |
| 2006/0116610 A1 | 6/2006 | Hare et al. |
| 2008/0171965 A1 | 7/2008 | Soltani et al. |
| 2008/0221506 A1* | 9/2008 | Rodriguez ............ A61N 7/00 604/22 |
| 2008/0294051 A1 | 11/2008 | Koshigoe et al. |
| 2009/0018472 A1 | 1/2009 | Soltani et al. |
| 2009/0143796 A1* | 6/2009 | Stulen .............. B06B 3/00 606/169 |
| 2010/0174170 A1 | 7/2010 | Razavi |
| 2010/0274269 A1 | 10/2010 | Song et al. |
| 2010/0331871 A1 | 12/2010 | Nield et al. |
| 2011/0004149 A1 | 1/2011 | Artsyukhovich et al. |
| 2011/0015631 A1 | 1/2011 | Weiner et al. |
| 2011/0046522 A1 | 2/2011 | Chan |
| 2011/0213397 A1 | 9/2011 | Mathonnet |
| 2011/0238057 A1 | 9/2011 | Moss et al. |
| 2011/0301506 A1 | 12/2011 | Volz |
| 2012/0016272 A1 | 1/2012 | Nita et al. |
| 2012/0157890 A1 | 6/2012 | Govari et al. |
| 2012/0163126 A1 | 6/2012 | Campbell et al. |
| 2012/0191115 A1 | 7/2012 | Gilbert |
| 2012/0209303 A1 | 8/2012 | Frankhouser et al. |
| 2012/0232435 A1 | 9/2012 | Nita et al. |
| 2012/0310230 A1 | 12/2012 | Willis |
| 2013/0253387 A1 | 9/2013 | Bonutti et al. |
| 2014/0128863 A1 | 5/2014 | Du et al. |
| 2014/0364775 A1 | 12/2014 | Du et al. |
| 2016/0175150 A1 | 6/2016 | Banko |
| 2016/0334262 A1 | 11/2016 | Haran et al. |
| 2017/0360501 A1 | 12/2017 | Branovan |
| 2019/0128851 A1 | 5/2019 | Wells |
| 2019/0328443 A1 | 10/2019 | Kevin et al. |

FOREIGN PATENT DOCUMENTS

| | | |
|---|---|---|
| EP | 1025806 B1 | 4/2006 |
| WO | WO 1999/044514 | 9/1999 |
| WO | WO 2005/072391 | 8/2005 |

(56) References Cited

FOREIGN PATENT DOCUMENTS

| WO | WO 2006/059966 | 6/2006 |
| WO | WO 2012/118018 | 9/2012 |
| WO | WO 2016/081026 A1 | 5/2016 |

OTHER PUBLICATIONS

"Design Considerations in Small-Diameter Medical Tubing," Jan. 1, 2001 [online] [Retrieved from the Internet] Retrieved from http://www.mddio9nline.com/print/181, Retrieved on Sep. 21, 2012.

Cyberwand™, Dual Probe Ultrasonic Lithotripter System, Cybersonics, Inc.

"Fundamentals of Ultrasonic Imaging and Flaw Detection," National Instruments tutorial, Feb. 11, 2010.

"Pebax® Tubing Grades," Applied Medical Tubing [online] [Retrieved from the Internet] Retrieved on www.appliedtubing.com/_mgxroot/page_10795.html, Retrieved on Nov. 1, 2012.

Pagnani, C. et al., "Prevention of stone migration with the Accordion during endoscopic ureteral lithotripsy," J Endourology, 26(5):484-488 (May 2012).

Examination Report for European Application No. 21787158.1, mailed Sep. 19, 2024.

* cited by examiner

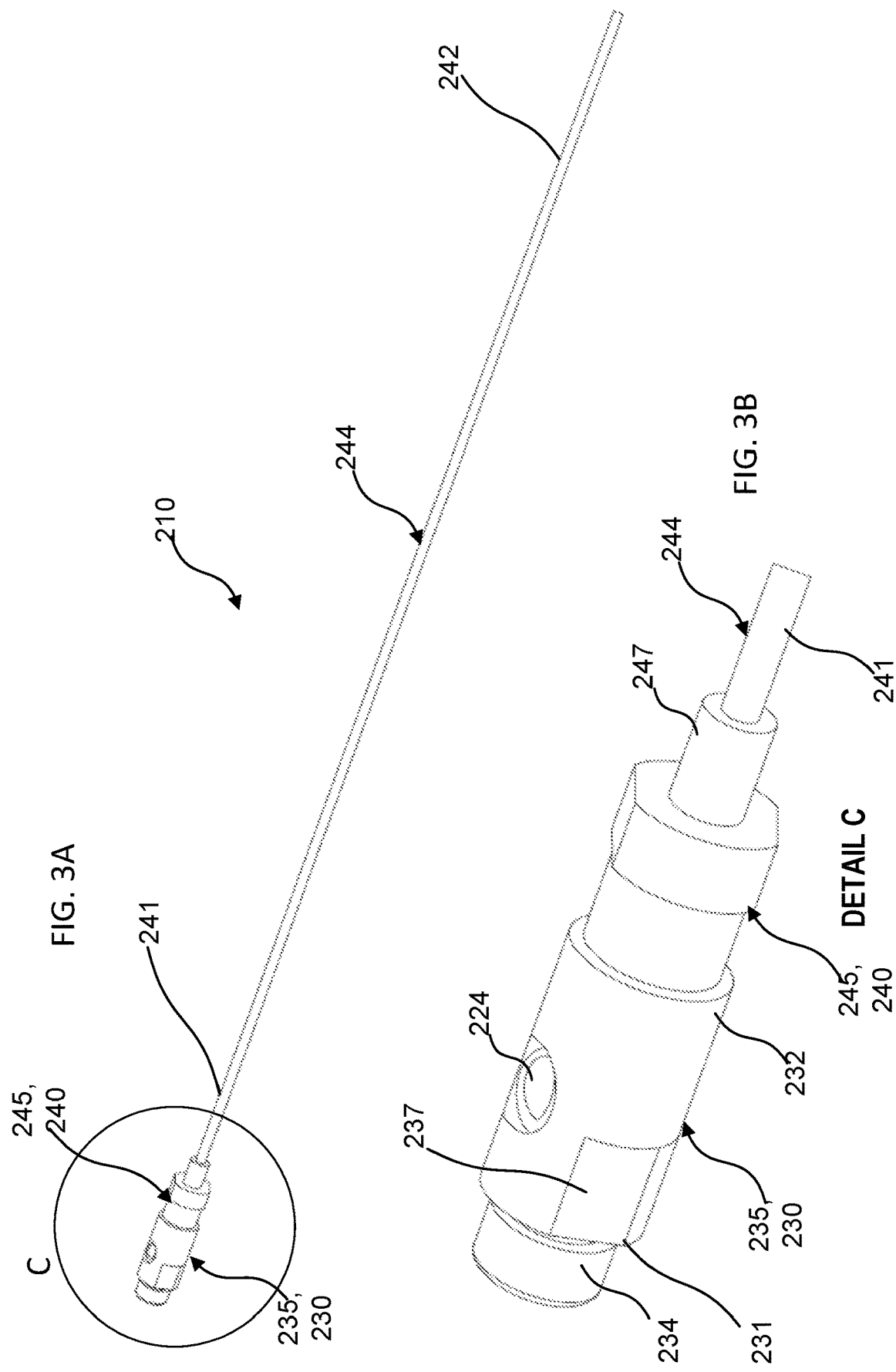

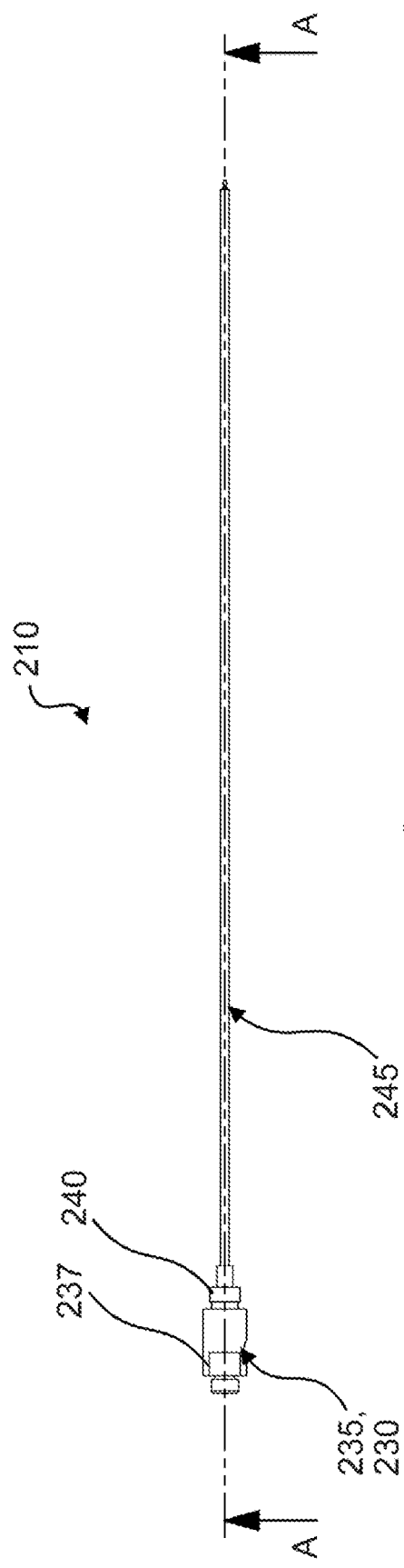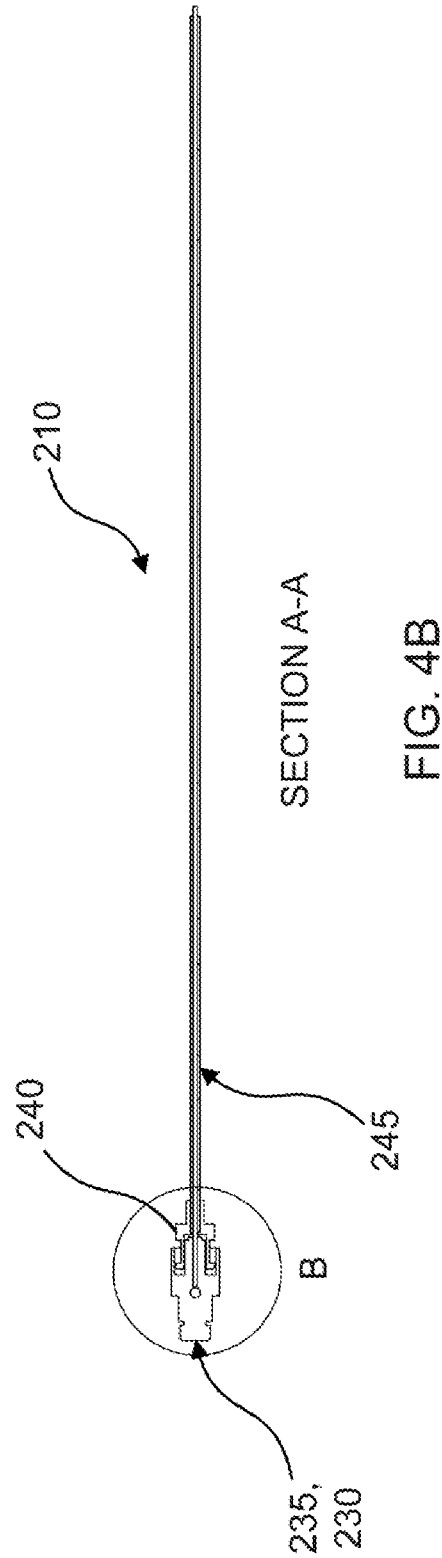
FIG. 4A
FIG. 4B  SECTION A-A

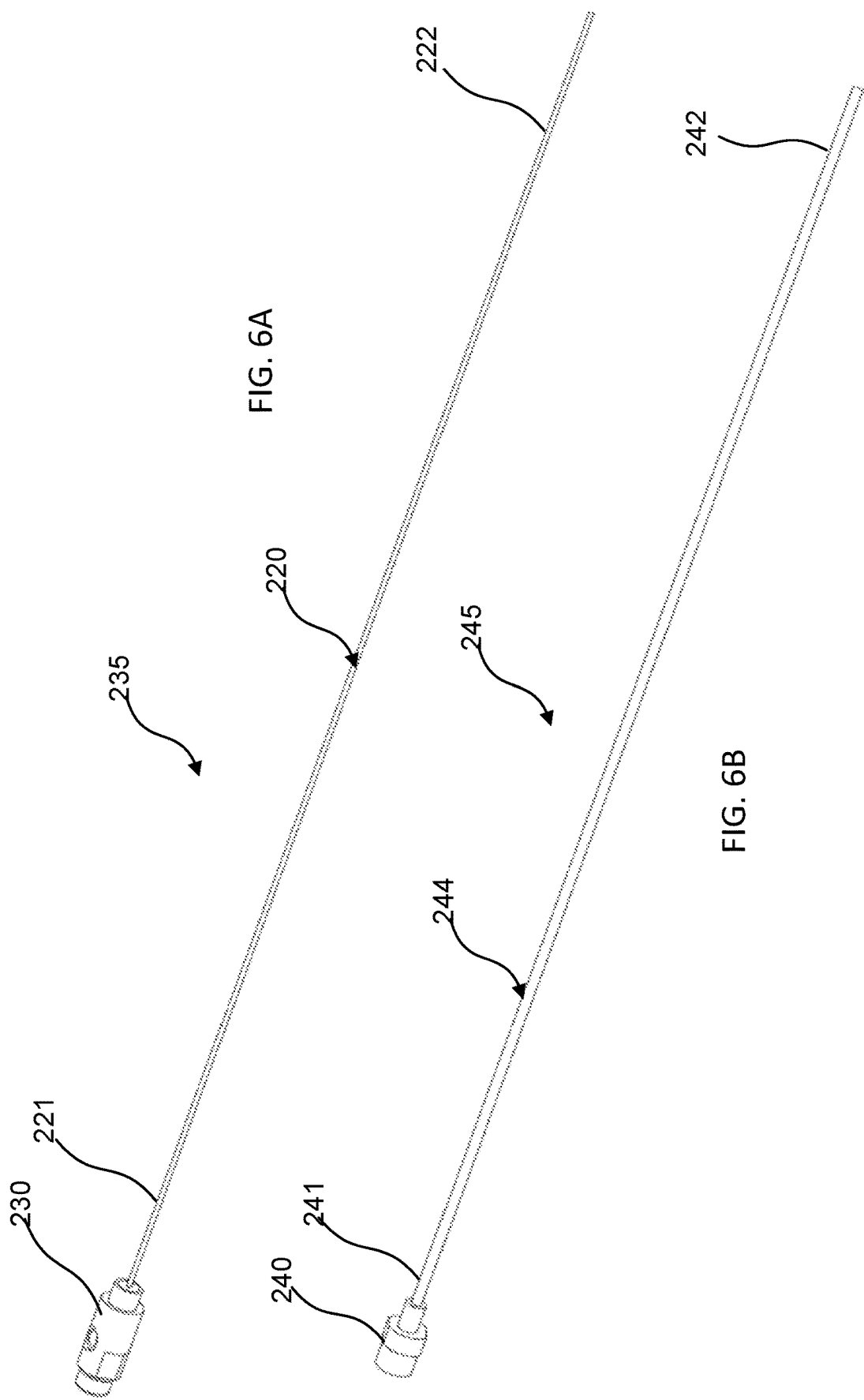

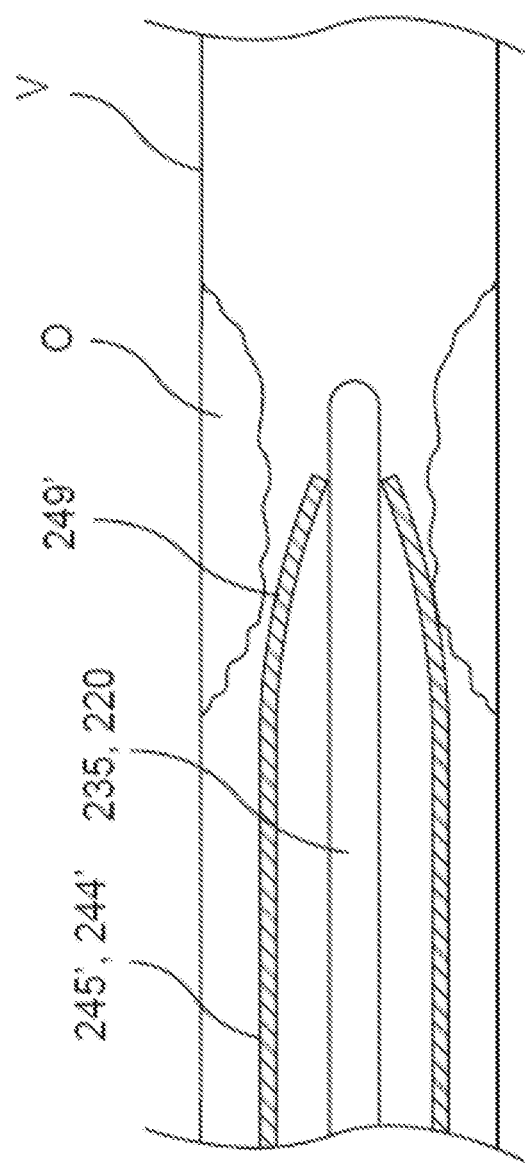

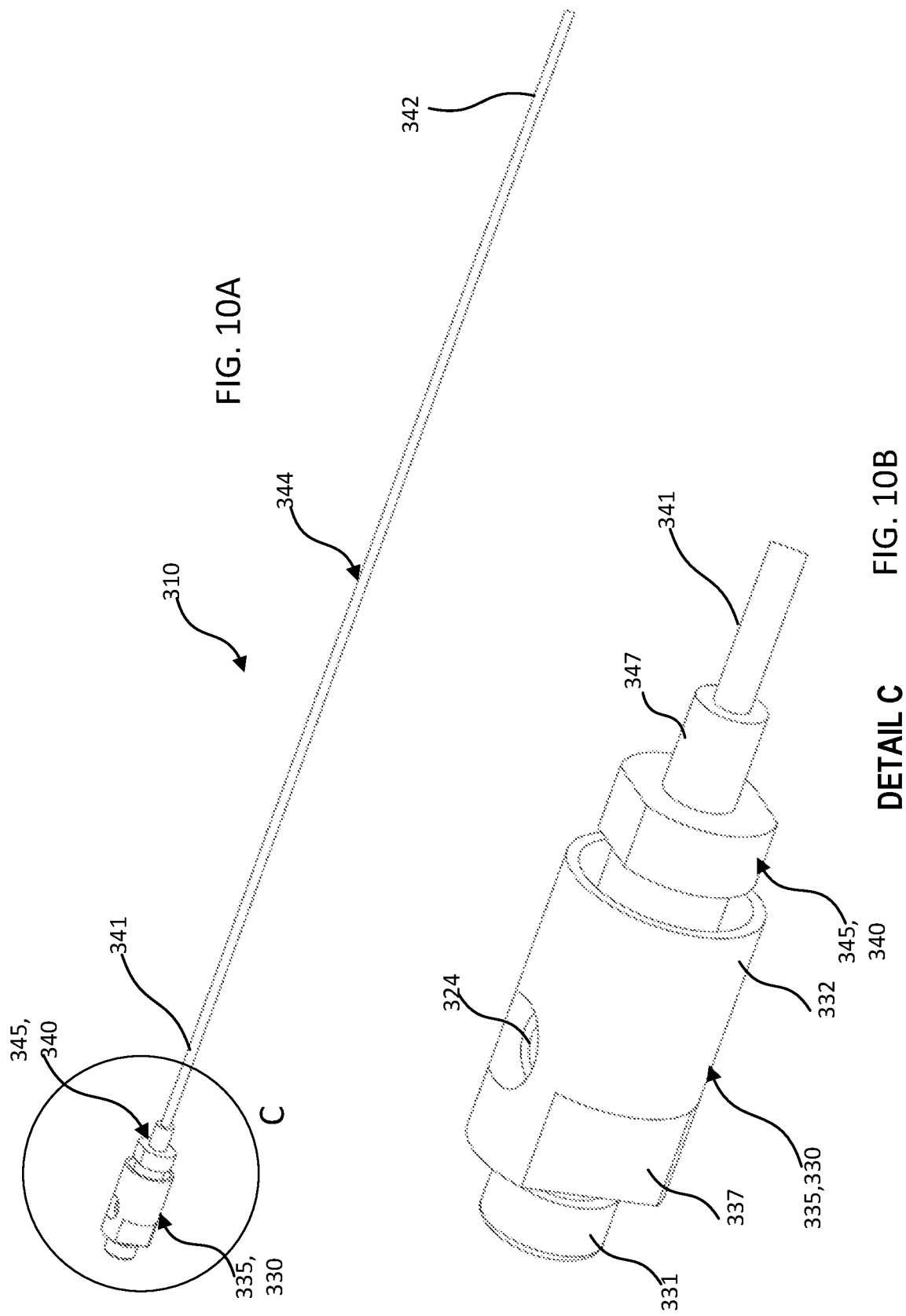

SECTION A-A

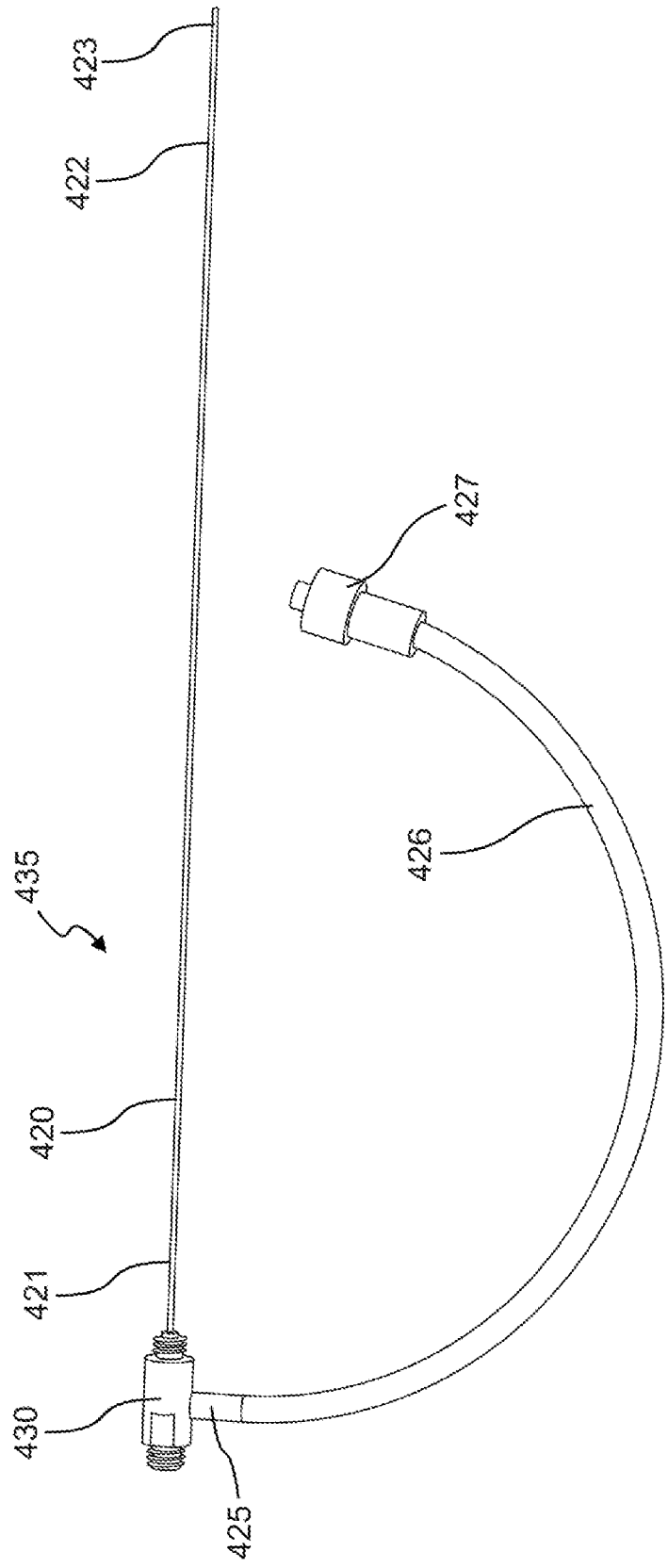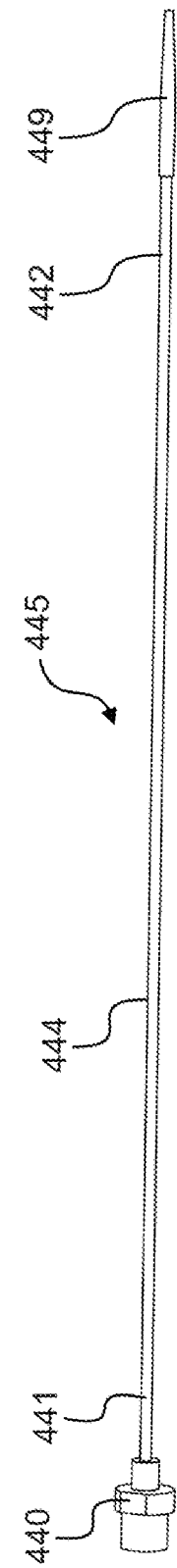
FIG. 15A
FIG. 15B

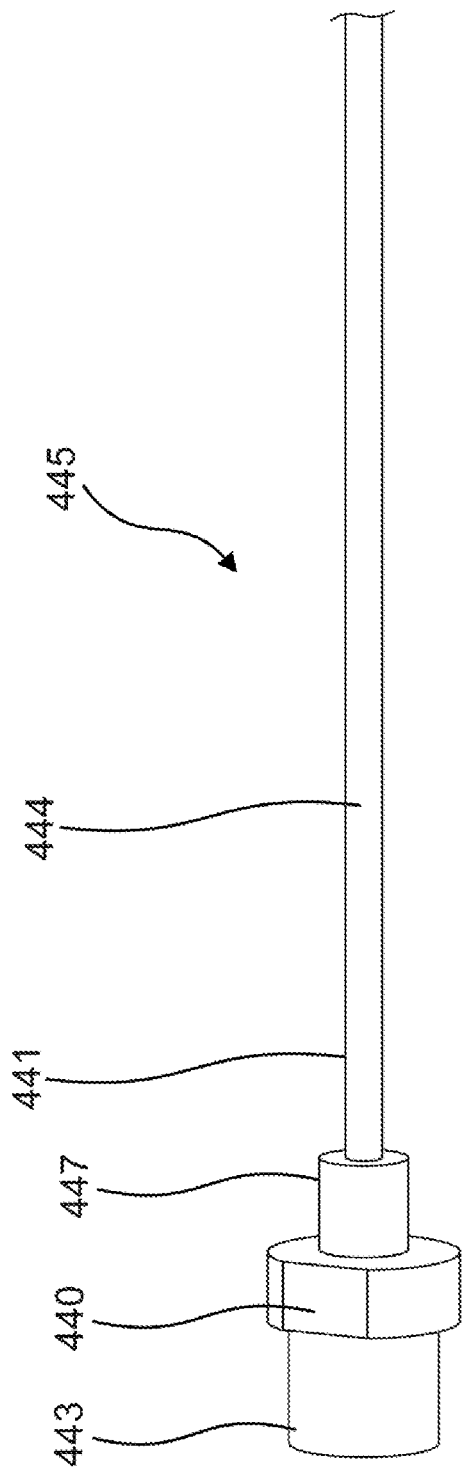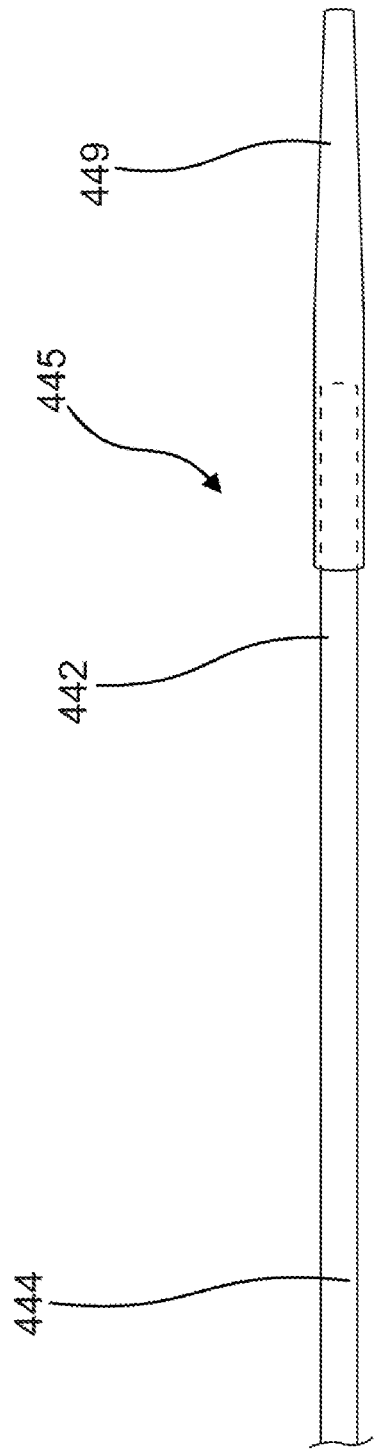
FIG. 18A
FIG. 18B

DUAL ULTRASONIC CATHETER AND METHODS OF USE

CROSS-REFERENCE TO RELATED APPLICATIONS

This application claims priority to and the benefit from U.S. Provisional Patent Application Ser. No. 63/140,372, filed Jan. 22, 2021, entitled "Dual Ultrasonic Probe and Methods of Use," the disclosure of which is incorporated herein by reference in its entirety.

BACKGROUND

The embodiments described herein relate generally to devices used in conjunction with an ultrasonic transducer assembly and, more specifically, to an ultrasonic probe assembly configured to transfer ultrasonic energy to a bodily tissue from an ultrasonic energy source.

Known ultrasonic energy transmission systems are used in many different medical applications, such as, for example, medical imaging, to disrupt obstructions and/or to ablate bodily tissue. In known ultrasonic energy transmission systems for tissue ablation, ultrasonic energy is transferred from an ultrasonic energy source through a transducer assembly (e.g., including an ultrasonic horn) and then to a transmission member, such as a wire or other elongate member, to a distal head. The transmission member can be, for example, an ultrasonic probe assembly. Ultrasonic energy propagates through the transmission member as a periodic wave thereby causing the distal head to vibrate. Such vibrational energy can be used to ablate or otherwise disrupt bodily tissue, for example, a vascular obstruction, a kidney stone or the like. To effectively reach various sites for treatment of intravascular occlusions or regions within the urinary tract, such ultrasonic transmission members often have lengths of about 65 cm or longer.

Known ultrasonic transmission members (e.g., prob assemblies) are constructed to be flexible enough to be passed through various bodily lumens, but also with sufficient strength to transmit ultrasonic energy to the distal tip (e.g., to ablate vascular or urinary obstructions). A stronger, more durable transmission member allows for greater transmission of energy but may not be flexible or thin enough to be advanced through the vasculature to a desired treatment area. A thinner transmission member can be more flexible but is less durable and more susceptible to breakage.

In an attempt to find a balance between strength and flexibility, some known ultrasonic transmission members have a reduced size or are less rigid, and therefore may not be well suited for treating occlusions (e.g., chronic total occlusion (CTO) within the vasculature). For example some known ultrasonic transmission members are too small to sufficiently expand against or deliver ultrasonic energy to the occlusion. Other known ultrasonic transmission members are not sufficiently rigid to penetrate the occlusion, thus limiting the effectiveness of delivering ultrasonic energy. Although some known systems include a lager guide catheter within which a transmission member can be placed, many known systems transmit energy via the inner transmission member to ablate the occlusion. Thus, in many instances, the energy transmitted from the inner transmission member is limited to a smaller portion of the occlusion.

Although some known systems include multiple transmission members through which energy (e.g., electrical energy) can be transmitted to ablate bodily tissue, such known systems do not provide for the ability to selectively transmit energy between the multiple transmission members. Further, such known systems may require the individual transmission members to each be separately coupled to an energy source.

Thus, a need exists for an improved apparatus and methods for transferring ultrasonic energy from an ultrasonic energy source to a bodily tissue. A need also exists for improved methods of ablating a chronic total occlusion (CTO) within the vasculature.

SUMMARY

Devices and methods of use of an ultrasonic probe assembly for use with an ultrasonic ablation system are described herein. In some embodiments, an apparatus includes a transducer assembly, a first probe, and a second probe. The transducer assembly includes a transducer housing and an ultrasonic transducer horn disposed within (or coupled to) the transducer housing. The transducer horn includes a probe coupling. The first probe includes a first coupler and a first elongate member coupled to the first coupler. The first coupler has a first coupling portion and a second coupling, portion, and the first coupling portion is configured to be releasably coupled to the probe coupling of the transducer horn such that the first probe is coupled to the ultrasonic transducer. The second probe includes a second coupler and a second elongate member coupled to the second coupler. The second coupler has a third coupling portion releasably couplable to the second coupling portion of the first coupler such that the second probe is coupled to the Ultrasonic transducer.

In some embodiments, a method includes introducing a distal portion of an ultrasonic probe assembly into a vessel of a patient. The ultrasonic probe assembly can be coupled to an ultrasonic transducer assembly and includes a first probe and a second probe. The first probe includes a first coupler and a first elongate member coupled to the first couple, and is coupled to the transducer assembly via the first coupler. The second probe includes a second coupler and a second elongate member coupled to the second coupler and is releasably coupled to the first coupler such that the second probe is coupled to the ultrasonic, transducer assembly via the first probe. The distal portion of the ultrasonic probe assembly is moved through an obstruction in the vessel such that a distal end portion of the first elongate member penetrates the obstruction and a distal end portion of the second elongate member penetrates the obstruction. Ultrasonic energy is transmitted from the ultrasonic transducer assembly to the first probe and to the second probe such that ultrasonic energy is delivered through the first elongate member and the second elongate member to the obstruction.

In some embodiments, a method includes introducing a distal portion of an ultrasonic probe assembly into a vessel of a patient. The ultrasonic probe assembly can be coupled to an ultrasonic transducer assembly and includes a first probe and a second probe. The first probe includes a first coupler and a first elongate member coupled to the first coupler and is coupled to the ultrasonic transducer assembly via the first coupler. The second probe includes a second coupler and a second elongate member coupled to the second coupler and the second elongate member defines a lumen. The first elongate member is within the lumen of the second elongate member such that a first distal tip of the first elongate member extends through a second distal tip of the second elongate member and outside the lumen of the second elongate member. The second coupler is releasably coupled to the first coupler. The distal portion of the ultrasonic probe assembly is moved through an obstruction in the vessel such that at least the distal tip of the first elongate member penetrates the obstruction. Ultrasonic energy is transmitted from the ultrasonic transducer assembly to at least the first probe such that ultrasonic energy is delivered through at least the first elongate member to the obstruction. The first probe is removed from within the second probe. A third probe is inserted into the lumen of the second probe. The third probe includes a third coupler and a third elongate member coupled to the third coupler. The third elongate member has a third distal tip that is sized to limit movement of the third distal tip through the second distal tip of the second elongate member. The second probe and the third probe are positioned through the obstruction in the vessel. After inserting the third probe, the second coupler of the second probe is coupled to the third coupler of the third probe, which includes moving the second elongate member proximally relative to the third elongate member causing the second distal tip to engage the third distal tip and deform a distal portion of the second elongate member to produce a contact location between the third elongate member and the second elongate member. Ultrasonic energy is transmitted from the ultrasonic transducer assembly to at least the third probe. At least a portion of the ultrasonic energy is delivered from the third elongate member through the contact location and the second elongate member to the obstruction.

BRIEF DESCRIPTION OF THE DRAWINGS

FIG. 3A is a perspective view of an ultrasonic probe assembly, according to an embodiment.

FIG. 3B is an enlarged view of detail C in FIG. 3A.

FIG. 4A is a side view of the ultrasonic probe assembly of FIG. 3A.

FIG. 4B is a cross-sectional side view taken along line A-A in FIG. 4A.

FIG. 6A is a perspective view of an inner probe of the ultrasonic probe assembly of FIG. 3A.

FIG. 6B is a perspective view of an outer probe of the ultrasonic probe assembly of FIG. 3A.

FIG. 9A is a side view of a vessel of a patient with an obstruction, with a first and second ultrasonic probe assembly, according to an embodiment, shown inserted within the vessel near the obstruction and in a use configuration to apply ultrasonic energy to the obstruction.

FIG. 10A is a perspective view of an ultrasonic probe assembly, according to another embodiment.

FIG. 10B is an enlarged view of detail C in FIG. 10A.

FIG. 15A is side view of an inner probe of the ultrasonic probe assembly of FIG. 14.

FIG. 15B is side view of an outer probe of the ultrasonic probe assembly of FIG. 14.

FIG. 18A is a side view of a proximal end portion of the outer probe of the probe assembly of FIG. 14.

FIG. 18B is a side view of a distal end portion of the outer probe of the probe assembly of FIG. 14.

DETAILED DESCRIPTION

Figure 1:
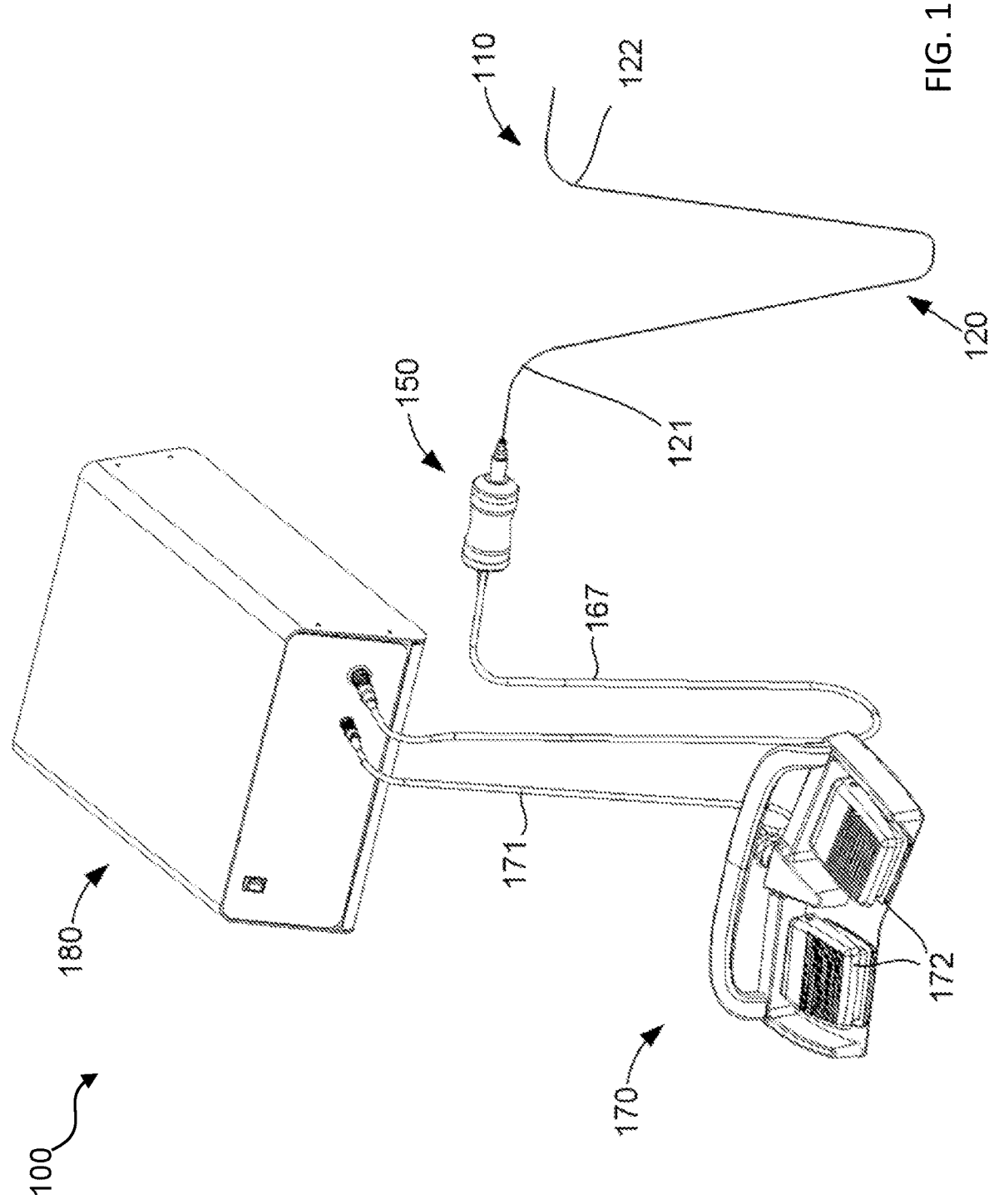
FIG. 1 is an illustration of a system for delivering ultrasonic energy to a bodily tissue according to an embodiment.

Devices and methods of use of an ultrasonic ablation system having a transducer assembly and an ultrasonic probe assembly that can be coupled thereto are described herein. The ultrasonic ablation system can be used to transfer ultrasonic energy to a bodily tissue from an ultrasonic energy source. For example, the ultrasonic ablation system can be used to transfer ultrasonic energy to an obstruction within a vessel of a patient. The vessel can be for example, a vein, artery, ureter, bile duct, etc.

In some embodiments, a transducer assembly includes a transducer horn and a transducer. The ultrasonic probe assembly can include a first probe and a second probe that can each be coupled to the transducer assembly to selectively couple the first probe and the second probe to the transducer and/or the transducer horn. Thus, the first probe and the second probe can each receive ultrasonic energy from the same transducer. The transducer can, for example, include one or more piezoelectric transducer members. In some embodiments, the transducer can include a stack of transducers (and can be referred to as an ultrasonic stack). The first and second probes can be coupled together in a coaxial or non-coaxial relationship to each other as described in more detail herein.

As used in this specification, the terms "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the terms "about" and "approximately" generally mean plus or minus 10% of the value stated. For example, about 0.5 would include 0.45 and 0.55, about 10 would include 9 to 11, about 1000 would include 900 to 1100.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

As used herein, the term "target tissue" refers to an internal or external tissue of or within a patient to which ultrasonic energy ablation techniques are applied. For example, a target tissue can be cancer cells, tumor cells, lesions, vascular occlusions, thrombosis, calculi, uterine fibroids, bone metastases, adenomyosis, or any other bodily tissue. Furthermore, the presented examples, of target tissues are not an exhaustive list of suitable target tissues. Thus, the ultrasonic energy systems described herein are not limited to the treatment of the aforementioned tissues and can be used on any suitable bodily tissue. Moreover, a "target tissue" can also include an artificial substance within or associated with a body, such as for example, a stent, a portion of an artificial tube, a fastener within the body or the like. Thus, for example, the ultrasonic energy systems described herein can be used on or within a stent or artificial bypass graft.

As used herein, the term "stiffness" relates to an object's resistance to deflection, deformation, and/or displacement produced by an applied force, and is generally understood to be the opposite of the object's "flexibility." For example, a wall of a tube with greater stiffness is more resistant to deflection, deformation and/or displacement when exposed to a force than a wall of a tube having a lower stiffness. Similarly stated, a tube having a higher stiffness can be characterized as being more rigid than a tube having a lower stiffness. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different than the portion of the object to which the force is directly applied. Said another way, in some objects, the point of deflection is distinct from the point where force is applied.

Stiffness (and therefore, flexibility) is an extensive property of the object being described, and thus is dependent upon the material from which the object is formed as well as certain physical characteristics of the object (e.g., cross-sectional shape, length, boundary conditions, etc.). For example, the stiffness of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be decreased, for example, by introducing into the object and/or constructing the object of a material having a relatively low modulus of elasticity.

The stiffness of an object can also be increased or decreased by changing a physical characteristic of the object, such as the shape or cross-sectional area of the object. For example, an object having a length and a cross-sectional area may have a greater stiffness than an object having an identical length but a smaller cross-sectional area. As another example, the stiffness of an object can be reduced by including one or more stress concentration risers (or discontinuous boundaries) that cause deformation to occur under a lower stress and/or at a particular location of the object. Thus, the stiffness of the object can be decreased by decreasing and/or changing the shape of the object.

Embodiments described herein relate to ultrasonic energy ablation systems. In such systems an ultrasonic probe assembly can be operably coupled to an ultrasonic energy source to deliver ultrasonic energy to a target tissue. For example, FIG. 1 is an illustration of an ultrasonic energy ablation system 100, according to an embodiment. The ultrasonic energy ablation system 100 (also referred to herein as "ultrasonic system" or "ultrasonic ablation system" or simply "system") includes an ultrasonic generator 180 (also referred to herein as "generator"), a foot switch 170, an ultrasonic transducer assembly 150, and an ultrasonic probe assembly 110 (also referred to herein as "probe assembly"). The ultrasonic generator 180 can be any suitable generator configured to generate, control, amplify, and/or transfer an electric signal (e.g., a voltage) to the transducer assembly 150.

The ultrasonic generator 180 includes at least a processor, a memory and the circuitry (not shown in FIG. 1) to produce an electronic signal (i.e., a current and a voltage) having the desired characteristics that can be received by the ultrasonic transducer assembly 150 and converted into ultrasonic energy. In some embodiments, the ultrasonic generator 180 can be electrically coupled to (e.g., "plugged into") an electric receptacle such that the ultrasonic generator 180 receives a flow of electric current. For example, in some embodiments, the ultrasonic generator 180 can be plugged into a wall outlet that delivers alternating current (AC) electrical power at a given voltage (e.g., 120V, 230V, or other suitable voltage) and a given frequency (e.g., 60 Hz, 50 Hz, or other suitable frequency).

Although not shown in FIG. 1, the ultrasonic generator 180 includes the electronic circuitry, hardware, firmware and or instructions to cause the ultrasonic generator 180 to act as a frequency inverter and/or voltage booster. In this manner, the ultrasonic generator 180 can produce and/or output a voltage to the transducer assembly 150 having the desired characteristics to produce the desired ultrasonic energy output. For example, in some embodiments, the ultrasonic generator 180 can receive AC electrical power at a frequency of approximately 60 Hz and a voltage of approximately 120 V and convert the voltage to a frequency up to approximately 20,000 Hz to 35,000 Hz with a voltage of approximately 500-1500 VAC (RMS). Thus, the ultrasonic generator 180 can supply the transducer assembly 150 with a flow of AC electrical power having an ultrasonic frequency.

As shown in FIG. 1, the system 100 can optionally include the foot switch 170 that is in electric communication with the ultrasonic generator 180 via a foot switch cable 171. The foot switch 170 includes a set of pedals 172 (e.g., two pedals as shown) that are operative in controlling the delivery of the ultrasonic electrical energy supplied to the ultrasonic transducer assembly 150. For example, in some embodiments, a user (e.g., a physician, technician, etc.) can engage and/or depress one or more of the pedals 172 to control the current supplied to the ultrasonic transducer assembly 150 such that, in turn, the probe assembly 110 delivers the desired ultrasonic energy to the bodily tissue, as further described in detail herein.

The transducer assembly 150 is in electric communication with the ultrasonic generator 180 via a transducer cable 167. In this manner, the transducer assembly 150 can receive an electrical signal (i.e., voltage and current) from the ultrasonic generator 180. The transducer assembly 150 is configured to produce and amplify the desired ultrasonic energy via a set of piezoelectric members 162 (i.e., piezoelectric rings) and a transducer horn 163 (see e.g., FIG. 2), and transfer the ultrasonic energy to the probe assembly 110 and/or the transmission member 120. The transducer assembly 150 can be any suitable assembly of the types shown and described herein.

Figure 2:
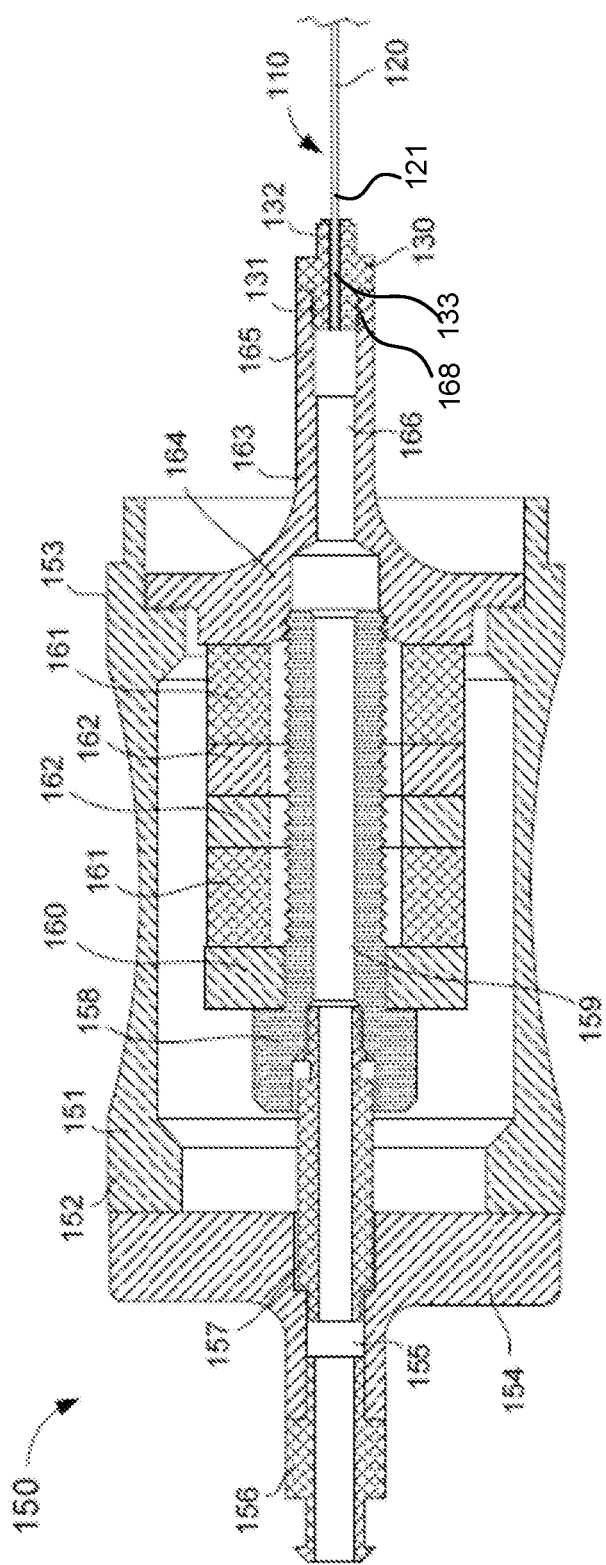
FIG. 2 is a cross-sectional view of an ultrasonic transducer included in the system of FIG. 1.
Figure 5:
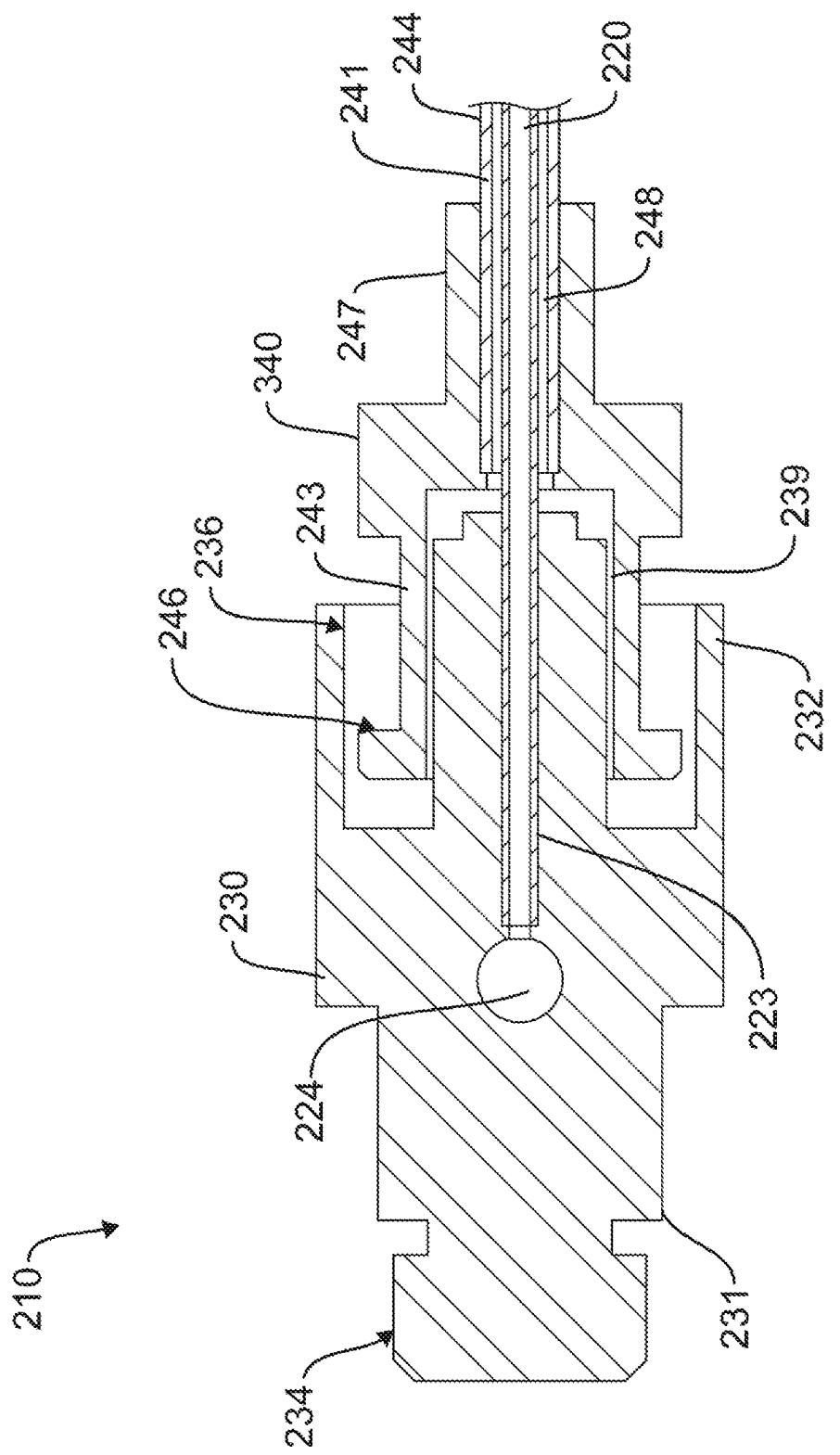
FIG. 5 is an enlarged view of detail B in FIG. 4B.

For example, in some embodiments, as shown in FIG. 2, the transducer assembly 150 includes a housing 151 having a proximal end portion 152 and a distal end portion 153. The housing 151 is configured to house or otherwise enclose at least a portion of a flow tube 157, a bolt 158, a back plate 160, a set of insulators 161, a set of piezoelectric rings 162 (the set of insulators and piezoelectric rings can be referred to as the ultrasonic stack), and a transducer horn 163.

The proximal end portion 152 of the housing 151 is coupled to a proximal cover 154 (e.g., via an adhesive, a press or friction fit, a threaded coupling, a mechanical fastener, or the like). The proximal cover 154 defines an opening 155 such that the proximal cover 154 can receive a portion of a connector 156 (e.g., a luer connector) on a proximal side thereof (e.g., substantially outside the housing 151) and a portion of the flow tube 157 on a distal side thereof (e.g., substantially inside the housing 151). Expanding further, the proximal cover 154 can receive the connector 156 and the flow tube 157 such that the proximal cover 154 forms a substantially fluid tight seal with the connector 156 and the flow tube 157. In this manner, a vacuum can be applied via the connector 156 to irrigate and/or aspirate the region of the body within which the probe assembly 110 is disposed. Similarly stated, this arrangement results in the connector 156 being placed in fluid communication with a lumen defined by the transmission member 120. Although the transducer assembly 150 is shown as including a flow path (and the connector 156) to facilitate irrigation and/or aspiration through the transducer assembly 150, in other embodiments, the flow path(s) for irrigation and/or aspiration need not be within the transducer assembly, but can instead be solely within other portions of the system (e.g., within the probe assembly).

The distal end portion 153 of the housing 151 is configured to receive the transducer horn 163 such that the transducer horn 163 is coupled to an inner surface of the housing 151. More specifically, the transducer horn 163 can be disposed at least partially within the housing 151 such that the transducer horn 163 can be moved relative to the housing 151 (e.g., when amplifying the ultrasonic energy), but not moved out of the housing 151 during normal use. The transducer horn 163 includes a proximal end portion 164 and a distal end portion 165 and defines a lumen 166 therethrough. The lumen 166 is configured to receive a portion of the bolt 158 at the proximal end portion 164 of the transducer horn 163 and a portion of the probe assembly 120 at the distal end portion 165 of the transducer horn 163, both of which are described in further detail herein.

As shown in FIG. 2, the back plate 160, the insulators 161, and the piezoelectric members 162 are disposed within the housing 151 and about the bolt 158. Thus, the piezoelectric members 162 and insulators 161 can be in the form of rings. More specifically, the arrangement of the back plate 160, the insulators 161, and the piezoelectric members 162 is such that the back plate 160 is disposed proximal to the insulators 161 and the piezoelectric members 162. The piezoelectric members 162 are each disposed between the insulators 161. Similarly stated, a first insulator 161 is disposed proximal to the piezoelectric members 162 and a second insulator 161 is disposed distal to the piezoelectric rings 162. The piezoelectric members 162 are in electric communication (e.g., via wires not shown in FIGS. 1 and 2) with the ultrasonic generator 180, as described in further detail herein.

As shown in FIG. 2, a portion of the bolt 158 is configured to be disposed within the lumen 166 defined by the transducer horn 163. More specifically, the portion of the bolt 158 forms a threaded fit with an inner surface of the transducer horn 163 that defines the lumen 166. In this manner, the bolt 158 can be advanced within the lumen 166 such that the bolt 158 exerts a compressive force on the backing plate 160, the insulators 161, and the piezoelectric members 162. Thus, the backing plate 160, the insulators 161, and the piezoelectric members 162 are retained between a head of the bolt 158 (e.g., at the proximal end) and a proximal surface of the transducer horn 163. The torque applied to the bolt and/or the clamping force exerted between the head of the bolt 158 and the proximal surface of the transducer horn 163 is such that that the deviation of the transducer natural frequency deviation is within ten percent from nominal. Therefore, in use, the piezoelectric members 162 can vibrate and/or move the transducer horn 163, as further described herein.

The bolt 158 further defines a lumen 159 such that a proximal end portion of the bolt 158 can receive a distal end portion of the flow tube 157. In this manner, the lumen 159 defined by the bolt 158 and the flow tube 157 collectively place the lumen 166 defined by the transducer horn 163 in fluid communication with the connector 156. Thus, the lumen 166 of the transducer horn 163 can be placed in fluid communication with a volume substantially outside of the proximal end of the housing 151.

As shown in FIGS. 1 and 2, the probe assembly 110 includes at least an elongate transmission member 120 (also referred to herein as "transmission member" or "elongate member") and a coupler 130. In some embodiments the probe assembly 110 can include multiple probes, each having an elongate member and a coupler. Such embodiments are described below. For example, in some embodiments, the transducer assembly 150 can be used with (or coupled to) the probe assembly 210. The coupler 130 includes a proximal end portion 131 and a distal end portion 132 and defines a lumen 133 that extends therethrough. The proximal end portion 131 of the coupler 130 is disposed within the lumen 166 at the distal end portion 165 of the transducer horn 163 and forms a threaded fit with a probe coupling 168 at the inner surface of the transducer horn 163 that defines the lumen 166. In this embodiment, the probe coupling 168 is a threaded coupling. The distal end portion 131 of the coupler 130 is configured to receive a portion of the transmission member 120 to fixedly couple the transmission member 120 to the coupler 130. In this manner, the probe assembly 110 can be removably coupled to the transducer assembly 150 via the coupler 130.

The transmission member 120 is an elongate tube having a proximal end portion 121 and a distal end portion 122. The transmission member 120 can be any suitable shape, size, or configuration and is described in further detail herein with respect to specific embodiments. In some embodiments, the transmission member 120 can optionally include any suitable feature configured to increase the flexibility (e.g., decrease the stiffness) of at least a portion of the transmission member 120, thereby facilitating the passage of the transmission member 120 through a tortuous lumen within a patient (e.g., a urinary tract, a vein, artery, etc.). For example, in some embodiments, a portion of the transmission member 120 can be formed from a material of lower stiffness than a different portion of the transmission member 120 formed from a material of greater stiffness. In some embodiments, the stiffness of at least a portion of the transmission member 120 can be reduced by defining an opening (e.g., notch, a groove, a channel, a cutout, or the like), thereby reducing the area moment of inertia of the portion of the transmission member 120.

In use, a user (e.g., a surgeon, a technician, physician, etc.) can operate the ultrasonic system 100 to deliver ultrasonic energy to a target bodily tissue within a patient. For example, the ultrasonic system 100 can be used to treat a chronic total occlusion (CTO) in a patient. The user can, for example, engage the pedals 172 of the foot switch 170 such that the ultrasonic generator 180 generates an alternating current (AC) and voltage with a desired ultrasonic frequency (e.g., 20,000 Hz). In this manner, the ultrasonic generator 180 can supply AC electric power to the piezoelectric rings 162. The AC electric power can urge the piezoelectric rings 162 to oscillate (e.g., expand, contract, or otherwise deform) at the desired frequency, which, in turn, causes the transducer horn 163 to move relative to the housing 151. Thus, with the probe assembly 110 coupled to the transducer horn 163, the movement of the transducer horn 163 vibrates and/or moves the probe assembly 110. In this manner, the distal end portion 122 of the transmission member 120 can be disposed with a portion of the patient adjacent to a target tissue such that the transmission member 120 transfers at least a portion of the ultrasonic energy to the target tissue (not shown in FIGS. 1 and 2). For example, in some embodiments, a distal tip of the transmission member 120 can impact a target tissue such as, for example, to break apart an occlusion. In some embodiments, the movement of the distal end portion 122 of the transmission member 120 is such that cavitations occur within the portion of the patient. In this manner, the cavitations can further break apart a target tissue. In some embodiments, the ultrasonic system 100 can optionally be used to aspirate and/or to supply irrigation to a target tissue site. For example, a portion of the probe assembly 110 can include a port coupled to a fluid line that can be used to supply irrigation or aspirate particles from an obstruction at the treatment site.

FIGS. 3A-6B illustrate an ultrasonic probe assembly 210 that can be used within an ultrasonic energy ablation system, such as system 100 described above. For example, the ultrasonic probe assembly 210 can be releasably coupled to the transducer assembly 150. In this embodiment, the probe assembly 210 includes a first probe 235 (see, e.g., FIGS. 5 and 6A), and a second probe 245 (see, e.g., FIGS. 5 and 6B) that can be releasably coupled to the first probe 235 as described in further details below. The first probe 235 includes a first elongate transmission member 220 (also referred to herein as "first transmission member" or "first elongate member" or "transmission member" or "elongate member") and a coupler 230. The coupler 230 includes a proximal end portion 231 and a distal end portion 232 and defines a central lumen 223 (see, e.g., FIG. 5) that extends at least partially through the coupler 230. The coupler 230 also defines a side lumen 224 in fluid communication with the central lumen 223. In some embodiments, a side port (e.g., similar to the side port 425 described below) can be coupled to and/or within the side lumen 224 to provide aspiration and/or irrigation through the first probe 235. For example, the side lumen can be coupled to and in fluid communication with a transfer line that can be used to supply irrigation or aspirate particles from an obstruction at the treatment site. An embodiment illustrating a fluid line is discussed below for probe assembly 410. In other embodiments, the coupler 230 need not include a side lumen, and can instead include only a central lumen therethrough that facilitates aspiration and/or irrigation. The proximal end portion 231 of the coupler 230 includes a first coupling portion 234 configured to be releasably coupled to a probe coupling (see e.g., the probe coupling 168 in FIG. 2) at the distal end portion of the transducer assembly (e.g., distal end portion 165 of transducer assembly 150). For example, the first coupling portion 234 can be a threaded coupling that is threadably coupled within the transducer assembly 150 to a mating threaded probe coupling 168 within a lumen 166 at the distal end portion 165 of the transducer horn 163. In this manner, the probe 235 can be removably coupled to the transducer assembly 150 via the coupler 230. The coupler 230 also includes two flat indented surfaces 237 that can be used to receive a tool to assist in securing the coupler 230 to the probe coupling. For example, a tool such as a medical wrench can clamp onto the surfaces 237 and used to tighten the coupler 230 to the probe coupling.

The distal end portion 232 of the coupler 230 is configured to receive a portion of the transmission member 220 (i.e., within the central lumen 223) to fixedly couple the transmission member 220 to the coupler 230. The transmission member 220 includes a proximal end portion 221 and a distal end portion 222. The proximal end portion 221 is fixedly coupled to the distal end portion 232 of the coupler 230. The distal end portion 222 is configured to be inserted into a body of a patient as described in more detail below. As described above, the first probe 235 also includes a second coupling portion 236 to releasably couple to the first probe 235 to the second probe 245.

The second probe 245 includes an elongate transmission member 244 (also referred to herein as "second transmission member" or "second elongate member" or "transmission member" or "elongate member") and a coupler 240. The coupler 240 includes a proximal end portion 243 and a distal end portion 247 and defines a lumen 239 (see, e.g., FIG. 5) that extends at least partially therethrough. The transmission member 244 includes a proximal end portion 241 and a distal end portion 242. The proximal end portion 241 is fixedly coupled to the distal end portion 247 of the coupler 240. The proximal end portion 243 of the coupler 240 includes a coupling portion 246 (also referred to herein as "third coupling portion") configured to be releasably coupled to the second coupling portion 236 of the first probe 235. Thus, the second probe 245 can be removably or releasably coupled to the transducer assembly 150 via the first probe 235 (e.g., via the coupler 230). In this manner, both the first probe 235 and the second probe 245 can be coupled to the same transducer assembly and be driven by the same ultrasonic transducer. More specifically, the lumen 248 of the second probe 245 can receive at least a portion of the first elongate member 220 of the first probe 235 and the coupler 230 can be releasably coupled to the coupler 240. The elongate member 220 of the first probe 235 can, for example, be inserted through the lumen 248 of the second elongate member 244 such that a distal end of the first elongate member 220 extends outside of the lumen 248. In this manner, the second elongate member 244 can function as a guide catheter, as described below. By extending distally outside of the lumen 248, the distal end portion 222 of the elongate member 220 can be advanced into the target tissue.

In this embodiment, the second coupling portion 236 is a quick release connector (e.g., a luer lock type connector) and the third coupling portion 246 of the second probe 245 is a mating quick release connector to provide a quick release connection between the first probe 235 and the second probe 245. In alternative embodiments, the second coupling portion 236 can be a threaded coupling and the third coupling portion 246 can be a threaded coupling to threadably couple the first probe 235 to the second probe 246. Such embodiments are described below with reference to probe assemblies 310 and 410. In some embodiments, the second probe 245 can also include a tapered distal end portion that can be incorporated into the second elongate member 244 or provided as a separate component. Such an embodiment is discussed below with reference to probe assembly 410, which includes a tapered distal end portion 449, or for the alternative second probe 245' (shown in FIGS. 9A-9C), which includes a tapered distal end portion 249'. In some embodiments, the tapered distal end portion of the second probe 245 can be angled between 30 and 40 degrees relative to a centerline of the second elongate member 244. The tapered distal end portion 249' of the second probe 245 can assist with insertion of the probe assembly 210 into a tissue to be treated. Moreover, as discussed with reference to FIGS. 9A-9C, the tapered distal end portion 249' can also facilitate desired deformation of the probe assembly to produce enhanced contact between the first probe and the second probe. This enhanced contact can lead to improved transmission of ultrasonic energy from the first (inner) probe to the target tissue.

The first elongate member 220 and the second elongate member 244 can each be any suitable shape, size, or configuration as described herein. In some embodiments, the elongate members 220 and 244 can optionally include any suitable feature configured to increase the flexibility (e.g., decrease the stiffness) of at least a portion of the transmission member 220, 244 thereby facilitating the passage of the elongate members 220, 244 through a tortuous lumen within a patient (e.g., a urinary tract, a vein, artery, etc.). For example, in some embodiments, a portion of the elongate members 220 and/or 244 can be formed from a material of lower stiffness than a different portion of the elongate member 220, 244 formed from a material of greater stiffness. In some embodiments, the stiffness of at least a portion of the elongate members 220 and/or 244 can be reduced by defining an opening(s) (e.g., notch, a groove, a channel, a cutout, or the like) in the elongate members 220 and/or 244 or providing openings within a braided material in which the elongate members 220 and/or 244 may be formed as described below, thereby reducing the area moment of inertia of the portion of the transmission members 220, 244.

Further, the first elongate member 220 can be formed with the same or different material than the second elongate member 244. In some embodiments, the second elongate member 244 is formed with a more flexible material than the first elongate member 220. In other words, first elongate member 220 has a stiffness greater than the second elongate member 244. In some embodiments, the second elongate member 244 is formed with a braided metal material. In some embodiments, the braided material is stainless steel (e.g., 304 stainless steel), Nitinol® (i.e., a nickel-titanium alloy), or other metal alloys having a density of, for example, 60-75 PPI (picks per inch of length) and a diamond and/or spiral pattern.

As described above for the previous embodiment, in use, a user (e.g., a surgeon, a technician, physician, etc.) can operate the ultrasonic system 100 (described above) to deliver ultrasonic energy to a target bodily tissue within a patient. For example, the ultrasonic system 100 and probe assembly 210 can be used to treat a chronic total occlusion (CTO) in a patient.

The probe assembly 210, having two ultrasonic probes (first probe 235 and second probe 245), allows the user to use both the first probe 235 and the second probe 245 to treat the target object, or the user can selectively decouple the second probe 245 from the first probe 235 such that ultrasonic energy is transferred only to the first elongate member 220. In such a use, the second probe 245 can function, for example, as a guide catheter. The user can also selectively couple and decouple the second probe 245 from the first probe 235 while the probe assembly 210 is inserted within the patient's body. For example, in some instances, a user can connect the first probe 235 to the transducer assembly and use the second probe 245 as a guide catheter for inserting the first probe 235 into the patient's body. Ultrasonic energy can be provided via the transducer of the transducer assembly to the first probe and to a target tissue to be treated. The user can then connect the second probe 245 to the first probe 235 (via the coupler 230 and the second coupler 240) thereby connecting the second probe 245 to the transducer assembly and transducer, and apply ultrasonic energy through both probes to the target tissue. In some instances, the second probe 245 may not be used. In some instances, both the first probe 235 and the second probe 245 are coupled to the transducer and ultrasonic energy is applied through both probes to the target tissue.

When at least the first probe 235 of the probe assembly 210 is coupled to the transducer assembly 150 (instead of the probe assembly 110), the first elongate member 220 can receive ultrasonic energy from the ultrasonic transducer (e.g., piezoelectric members 162) of the transducer assembly 150 and convey the ultrasonic energy to a target object within a patient's body. Similarly, when the second probe 245 is coupled to the first probe 235, the second elongate member 244 can receive ultrasonic energy from the ultrasonic transducer and convey the ultrasonic energy to the target object within the patient's body. Because the second (outer) probe 245 has a larger diameter, conveying the ultrasonic energy through the second probe 245 can produce a larger opening through the target tissue (e.g., CTO).

As described above, the user can, for example, engage the pedals 172 of the foot switch 170 such that the ultrasonic generator 180 generates an alternating current (AC) and voltage with a desired ultrasonic frequency (e.g., 20,000 Hz). In this manner, the ultrasonic generator 180 can supply AC electric power to the piezoelectric members 162. The AC electric power can urge the piezoelectric members 162 to oscillate (e.g., expand, contract, or otherwise deform) at the desired frequency, which, in turn, causes the transducer horn 163 to move relative to the housing 151. Thus, with the probe assembly 210 coupled to the transducer horn 163, the movement of the transducer horn 163 vibrates and/or moves the probe assembly 210, and more specifically, the first elongate member 220 and/or the second elongate member 244 when they are coupled to the transducer assembly 150.

In use, the distal end portion of the probe assembly 210 can be inserted within a vessel of a patient adjacent to or penetrating a target tissue (e.g., an obstruction, such as a CTO) such that the first elongate member 220 or the first elongate member 220 and the second elongate member 244 can transfer at least a portion of the ultrasonic energy to the target tissue. The distal end portion of the probe assembly 220 can be inserted into the vessel either before or after coupling the first probe 235 and/or second probe 245 to the transducer assembly. In some embodiments, a distal tip or end of the first elongate member 220 can extend outside of the lumen 248 of the second elongate member 244 and impact a target tissue such as, for example, to break apart an occlusion. In some embodiments, movement of the distal end portion 222 of the first elongate member 220 is such that cavitations occur within the portion of the patient. In this manner, the cavitations can further break apart a target tissue. As described herein, in some embodiments, the probe assembly 210 can optionally be used to aspirate and/or to supply irrigation to a target tissue site. For example, the port of the first probe can be coupled to a transfer line that can be used to supply irrigation or aspirate particles from an obstruction at the treatment site.

Figure 7A:
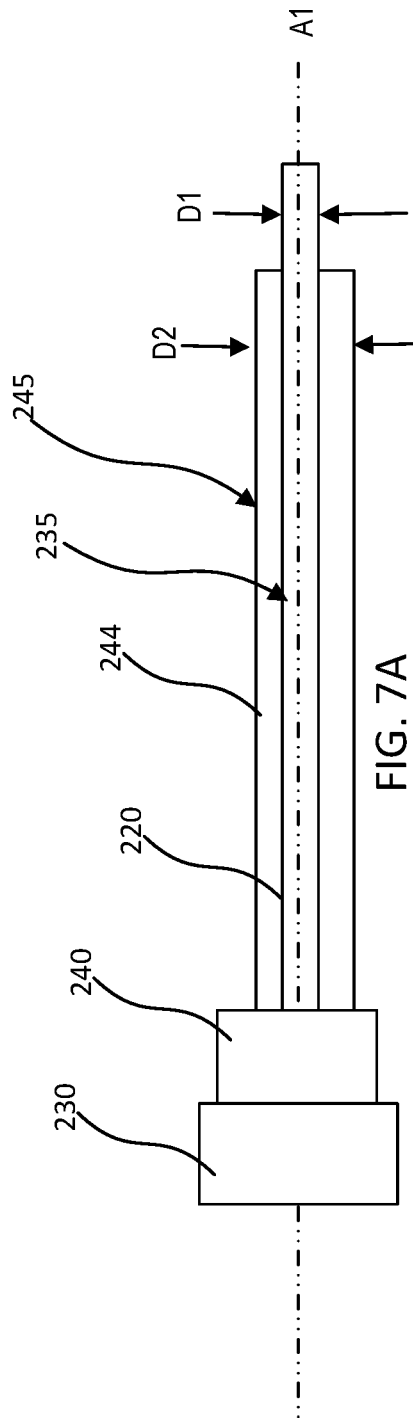
FIG. 7A is a schematic illustration of an inner probe and an outer probe of an ultrasonic probe assembly, according to an embodiment.

In some embodiments, the first elongate member 220 is coaxial with the second elongate member 244 when the first elongate member 220 is disposed at least partially within the lumen 248 of the second elongate member 244, as shown schematically, for example in FIG. 7A. As shown in FIG. 7A, the first elongate member 220 of the first probe 235 and the second elongate member 244 of the second probe 245 share a common center axis A1 (e.g., they are disposed coaxially). Further, the first elongate member 220 has a diameter D1 and the second elongate member 244 has a diameter D2 that is greater than the diameter D1, allowing the first elongate member 220 to be inserted through the second elongate member 244.

Figure 7B:
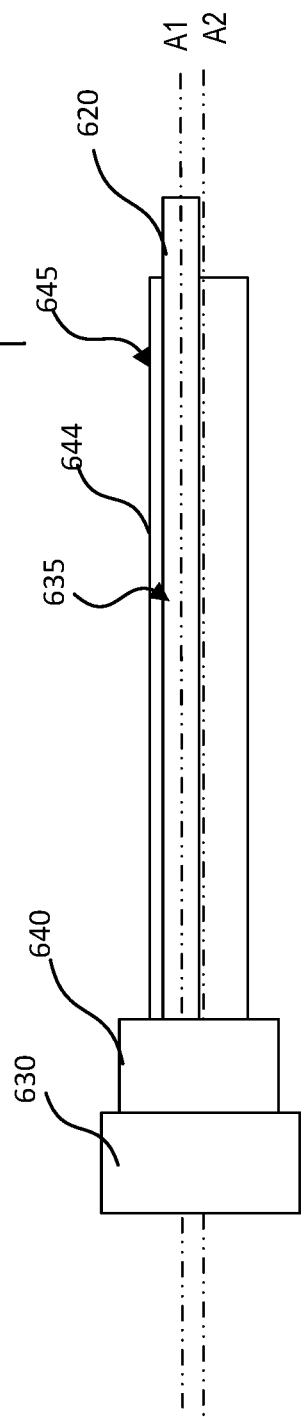
FIG. 7B is a schematic illustration of an inner probe and an outer probe of an ultrasonic probe assembly according to another embodiment.

In some embodiments, a first elongate member can be non-coaxial within the second elongate member when the first elongate member is disposed at least partially within the lumen of the second elongate member. This arrangement is shown schematically, for example in FIG. 7B. As shown in FIG. 7B, a first probe 635 includes a first coupler 630 coupled to a first elongate member 620 that has a first center axis A1 and a second probe 645 includes a second coupler 640 coupled to second elongate member 644 that has a second axis A2 that is offset from the first center axis A1. In other words, the first elongate member 620 is non-coaxial with the second elongate member 644. In such a non-coaxial configuration, the close proximity, or in some cases contact, between the first elongate member 620 and the second elongate member 644, allows for ultrasonic energy to be transferred from the first elongate member 620, to the second elongate member 644 and then to the target tissue, providing a greater amount of ultrasonic energy at the treatment site.

Figure 7C:
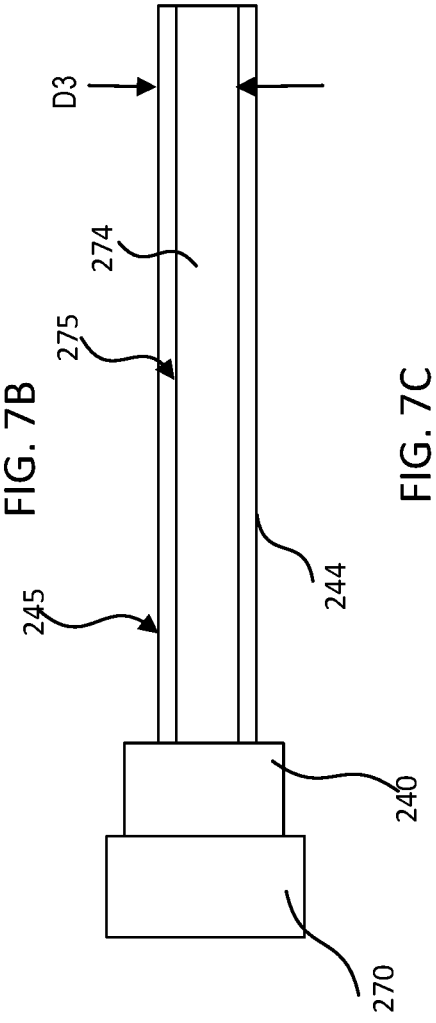
FIG. 7C is a schematic illustration of an inner probe and an outer probe of an ultrasonic probe assembly according to yet another embodiment.

Although the probe assembly 210 is described as including two probes (the first probe 235 and the second probe 245), in other embodiments, a probe assembly 210 can include any number of probes. For example, in some embodiments, a probe assembly can include more than one "inner" probe. The different inner probes can have different sizes and/or characteristics to facilitate the desired procedure. For example, in some embodiments a probe assembly can have a third probe (i.e., a second "inner probe") that has a larger size (e.g., diameter of the elongate member) than the first probe. The increased size can facilitate better contact with the outer probe, thereby enhancing the transmission of ultrasonic energy from the inner probe to the outer probe (and therefore into the target tissue). FIG. 7C illustrates a third probe 275 that can be used with the probe assembly 210 or any other probe assemblies described herein. The third probe 275 includes a third elongate member 274 and a third coupler 270. The third elongate member 274 of the third probe 275 has a diameter D3 that is greater than the diameter D1. In some cases, the third elongate member 274 may have too large of a diameter to exit a distal end of the second elongate member 244. An example use of the third probe 275 is described below with reference to FIGS. 9A-9C.

Figure 8:
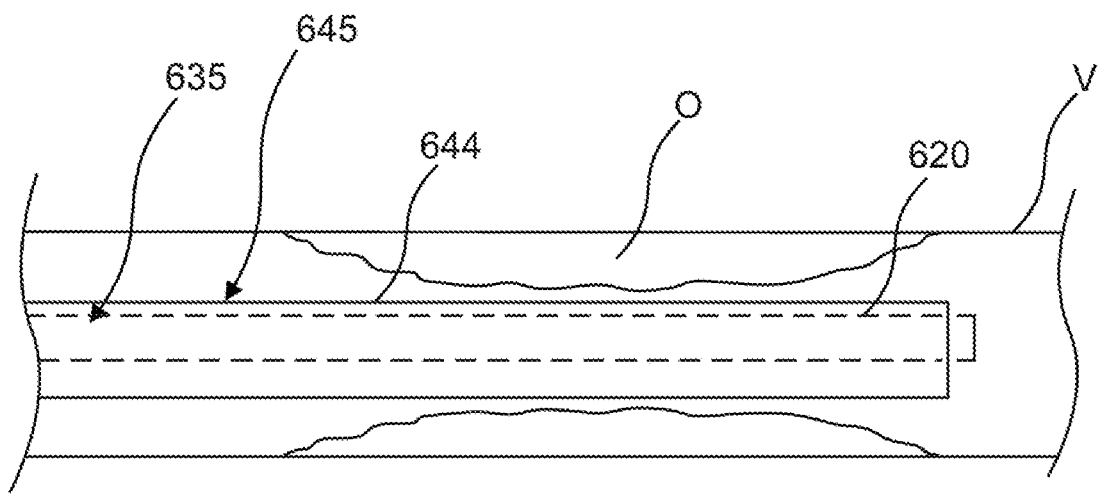
FIG. 8 is a schematic side view of a ultrasonic probe assembly, according to an embodiment, shown inserted within a vessel near an obstruction.

FIG. 8 is a schematic illustration of the first probe 635 and the second probe 645 (shown in FIG. 7B) disposed within a vessel V of a patient near an obstruction O. As described above, in this example illustration, the first probe 635 is disposed in a non-coaxial relationship with the second probe 645. With the distal portion of the probe assembly 610 inserted into the vessel V near the obstruction O, the transducer assembly can be actuated to deliver ultrasonic energy via the first elongate member 620 of the first probe 635 and the second elongate member 644 of the second probe 645 and into the obstruction.

Figure 9B:
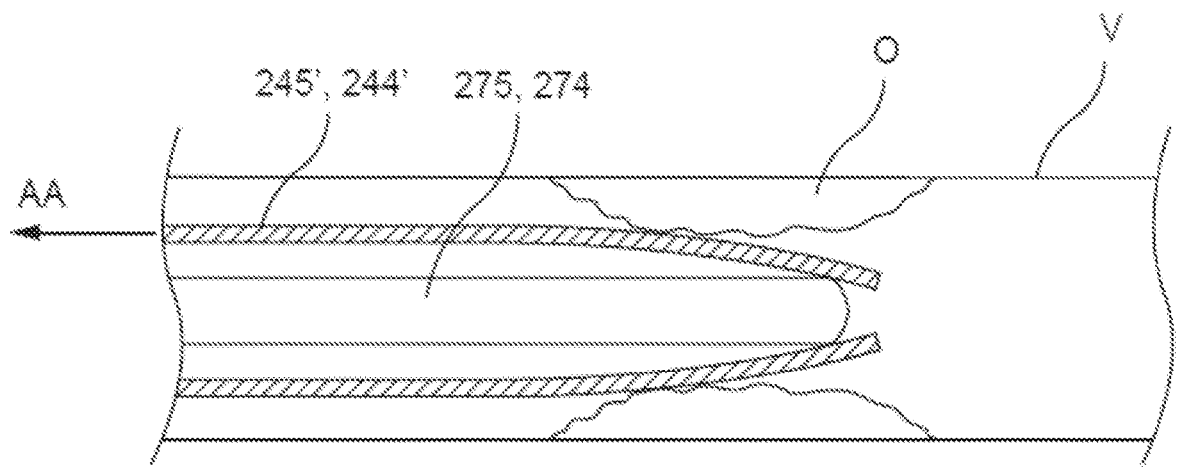
FIG. 9B is a side view of the vessel of FIG. 9A with a third ultrasonic probe assembly shown inserted within the first ultrasonic probe assembly in a first configuration near the obstruction.
Figure 9C:
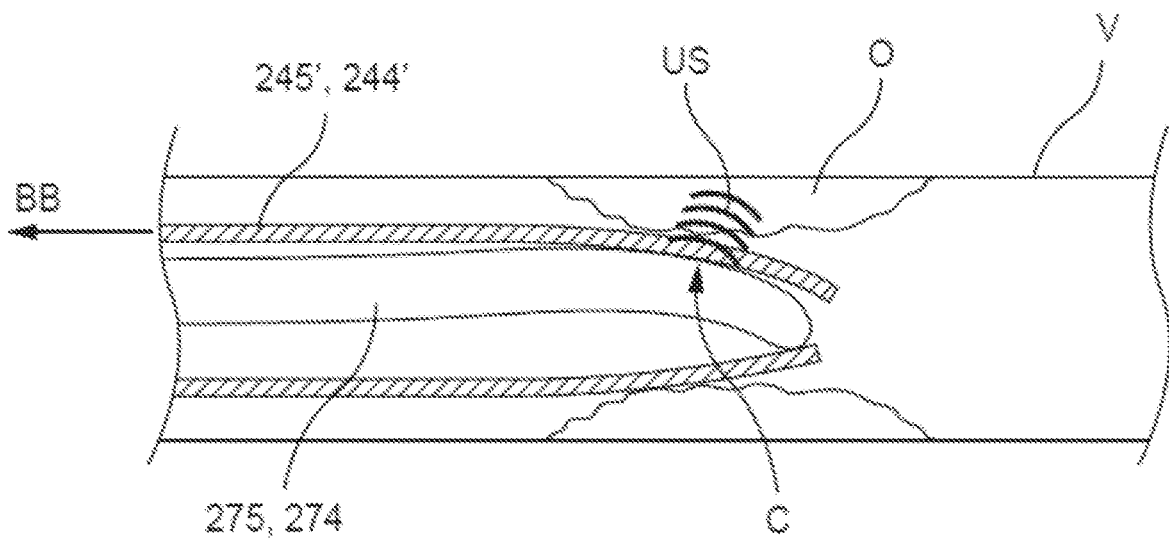
FIG. 9C is a side view of the vessel and third ultrasonic probe assembly of FIG. 9C in a second configuration near the obstruction to apply ultrasonic energy to the obstruction.
Figure 11A:
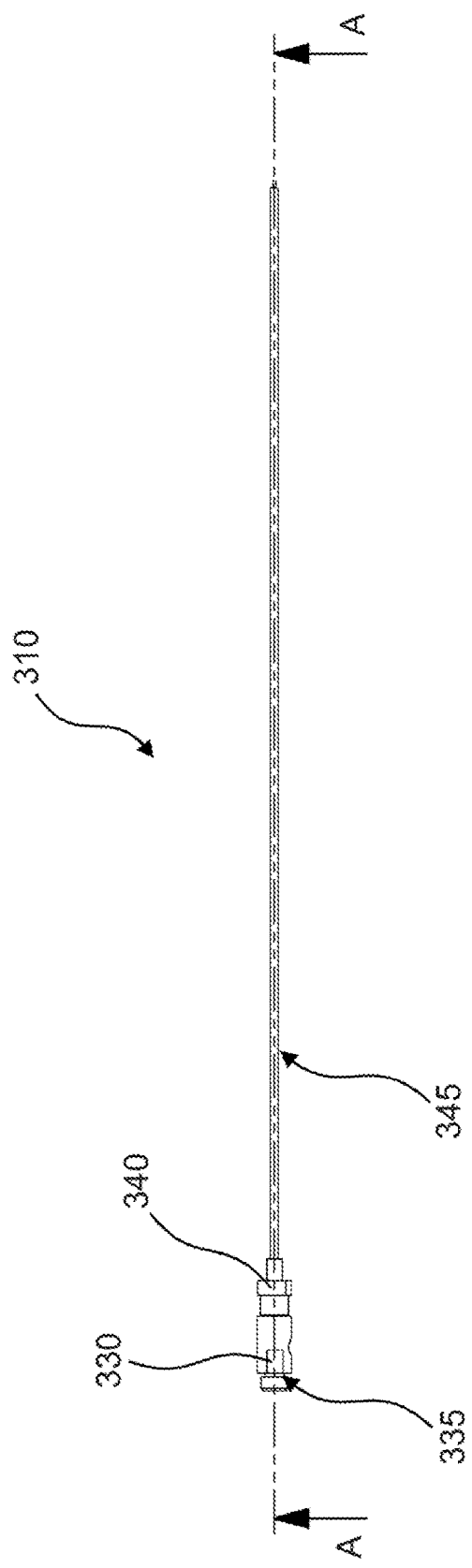
FIG. 11A is a side view of the ultrasonic probe assembly of FIG. 10A.
Figure 11B:
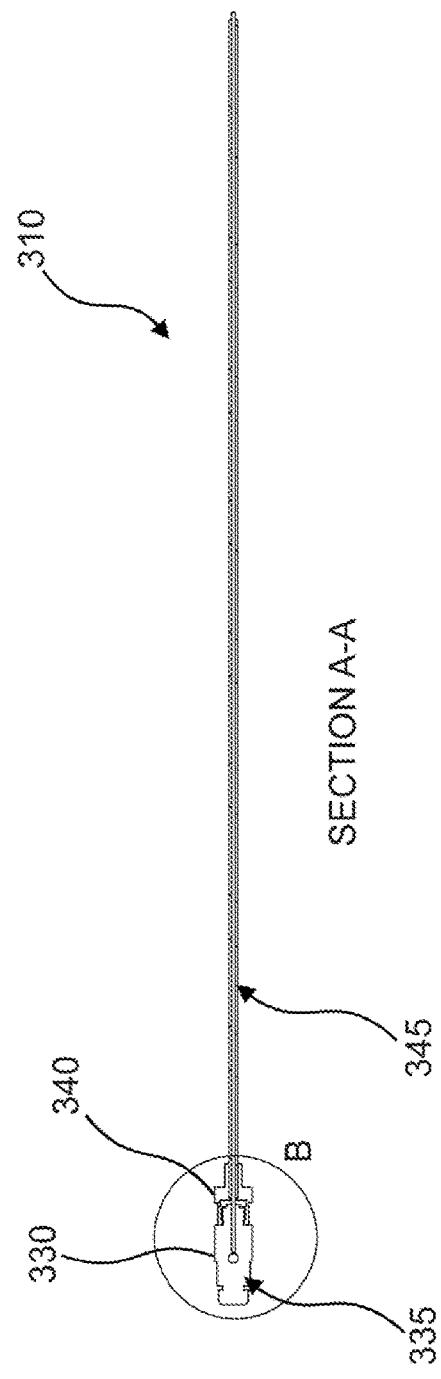
FIG. 11B is a cross-sectional side view taken along line A-A in FIG. 11A.
Figure 12:
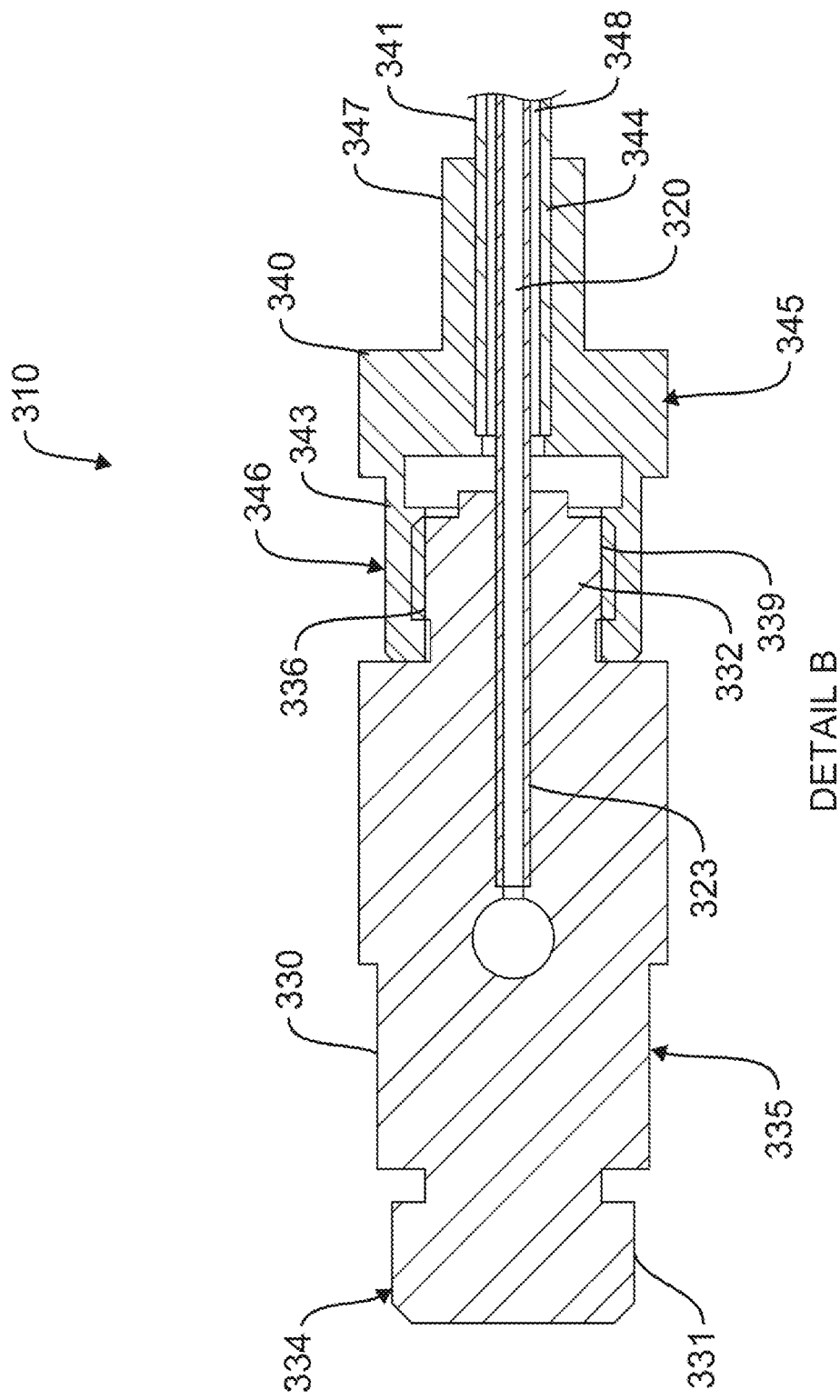
FIG. 12 is an enlarged view of detail B in FIG. 10B.
Figure 13:
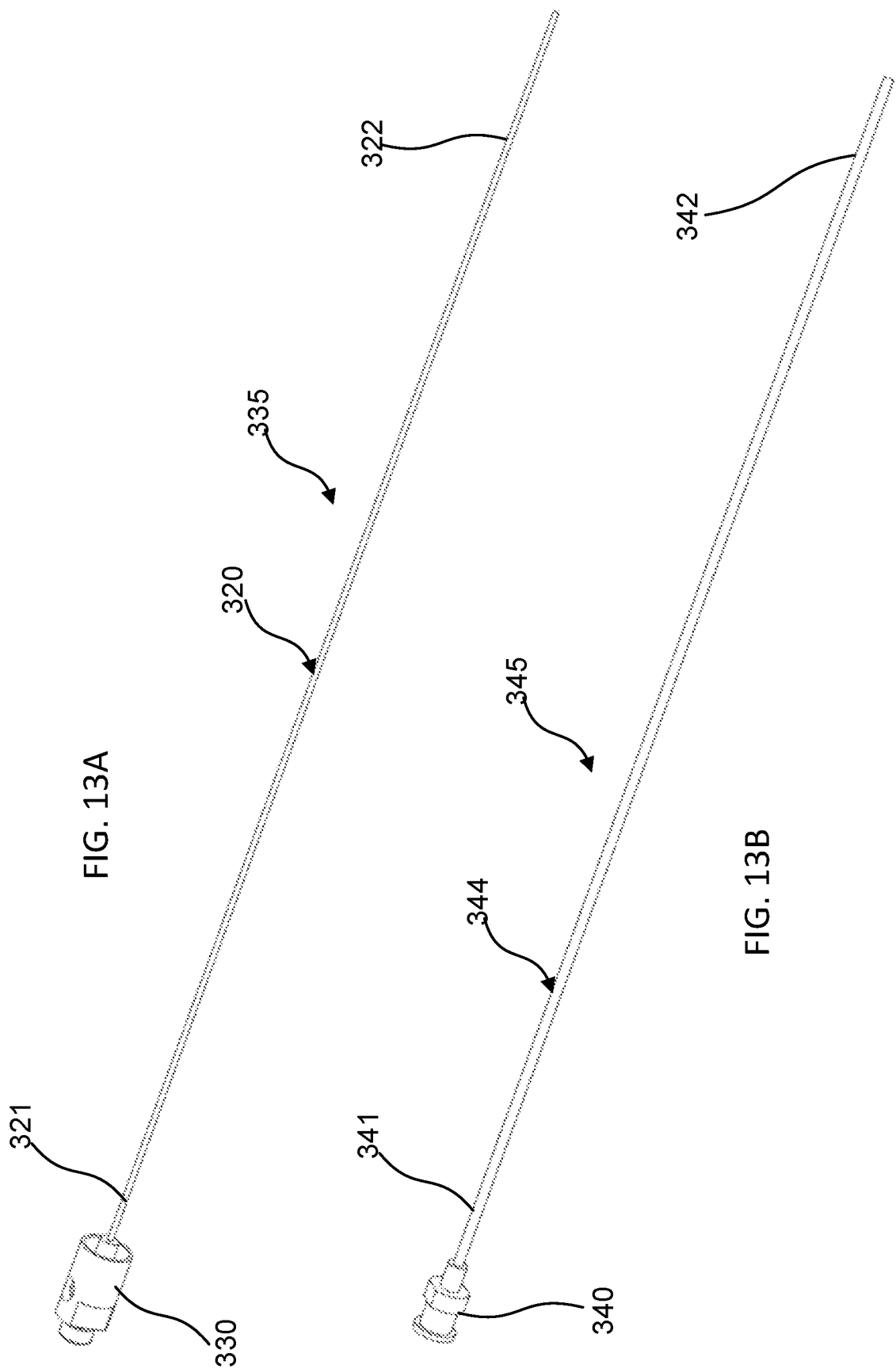
FIG. 13A is a perspective view of an inner probe of the ultrasonic probe assembly of FIG. 8A.
FIG. 13B is a perspective view of an outer probe of the ultrasonic probe assembly of FIG. 8A.
Figure 14:
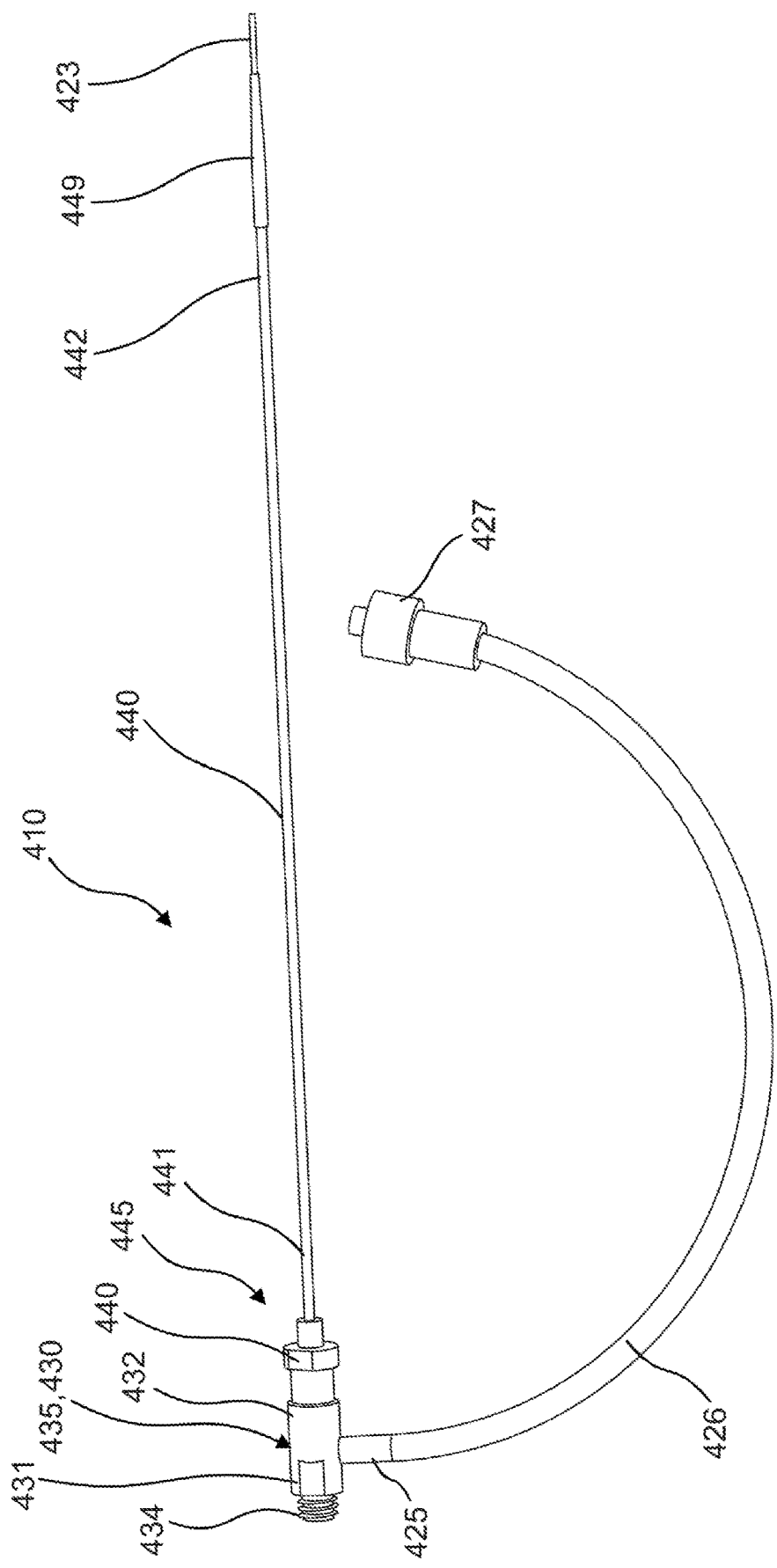
FIG. 14 is a side view of an ultrasonic probe assembly, according to another embodiment.
Figure 16:
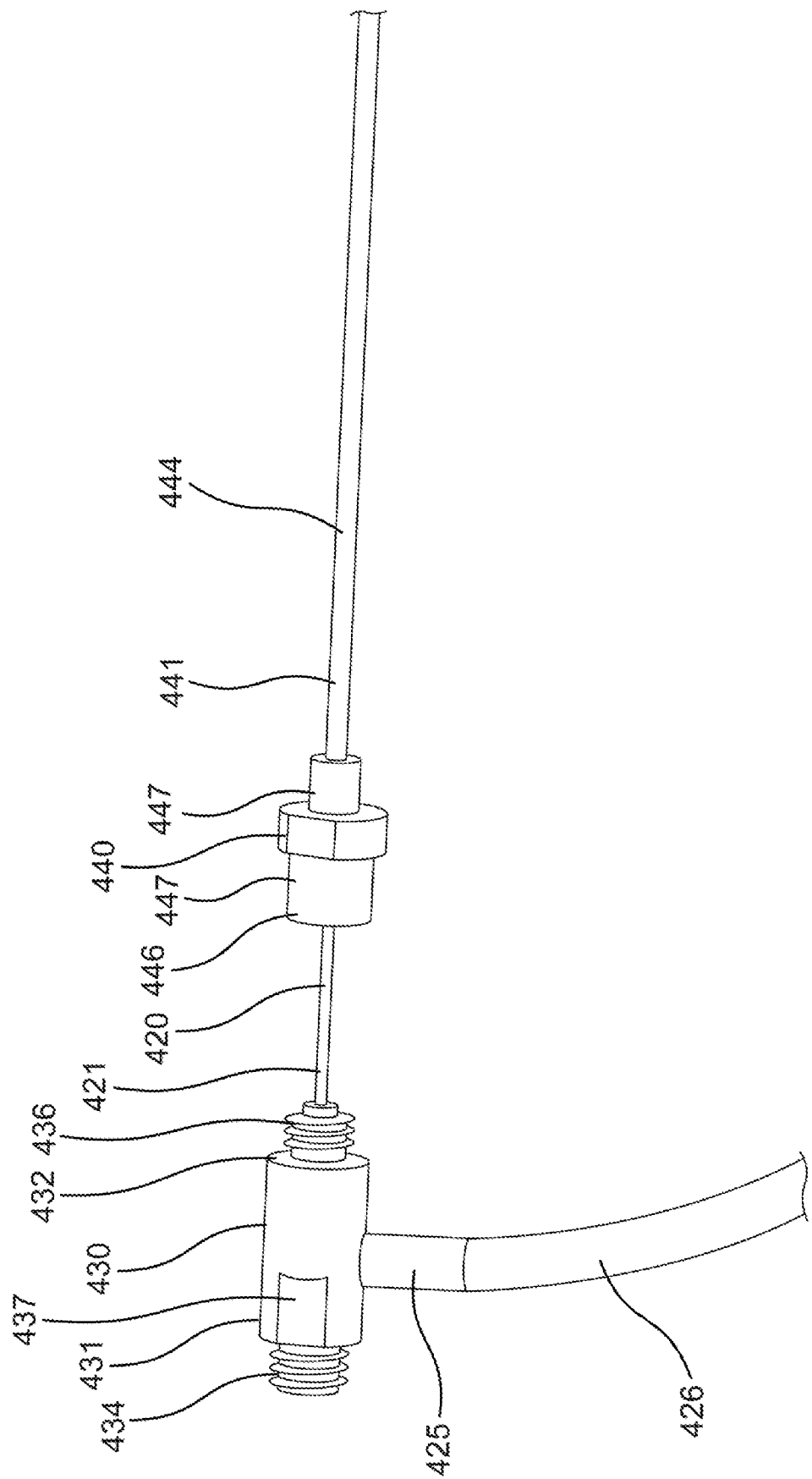
FIG. 16 is a side view of a proximal end portion of the probe assembly of FIG. 14 with the outer probe disconnected from the inner probe.
Figure 17A:
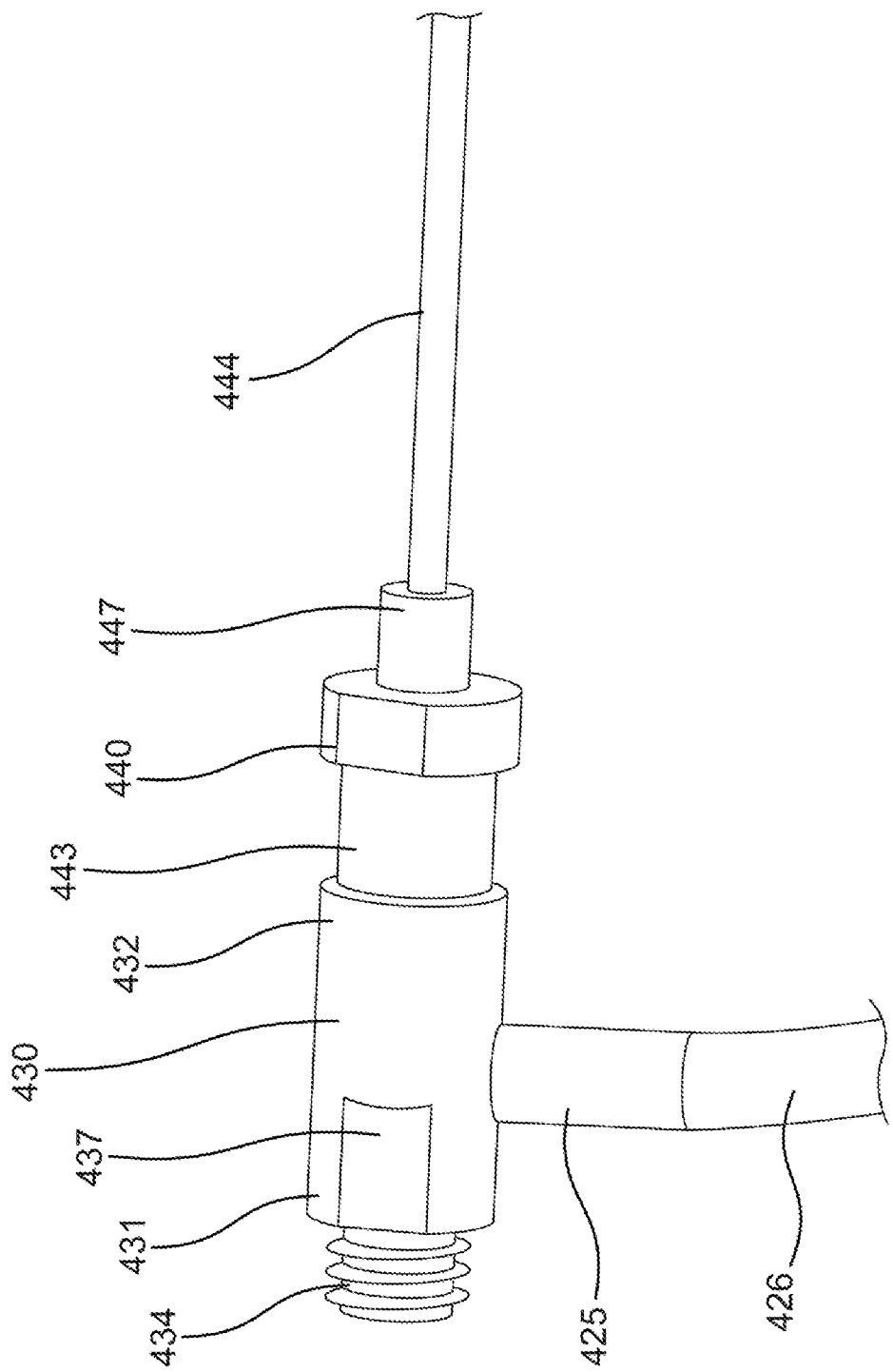
FIG. 17A is a side view of a proximal end portion of the probe assembly of FIG. 14 with the outer probe connected to the inner probe.
Figure 17B:
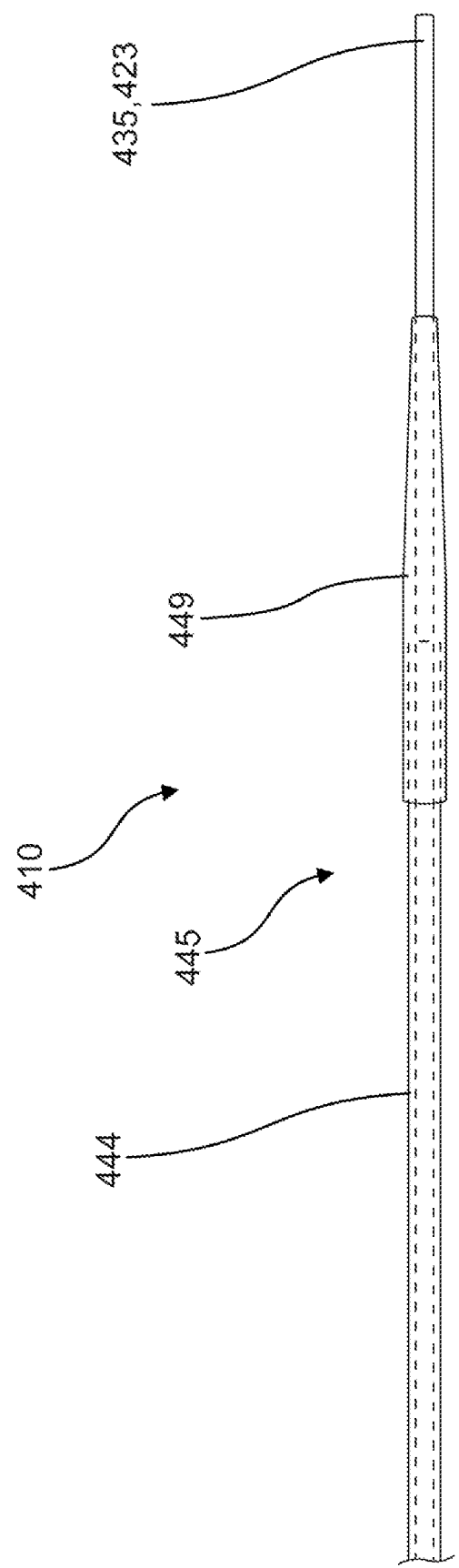
FIG. 17B is a side view of a distal end portion of the probe assembly of FIG. 14.
Figure 18C:
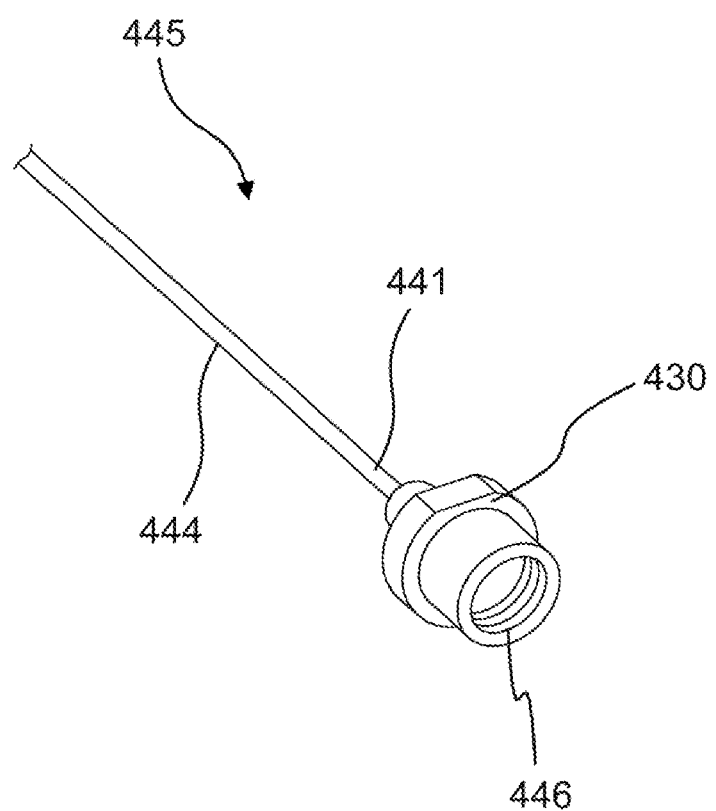
FIG. 18C is a proximal end perspective view of the outer probe of the probe assembly of FIG. 14.
Figure 19:
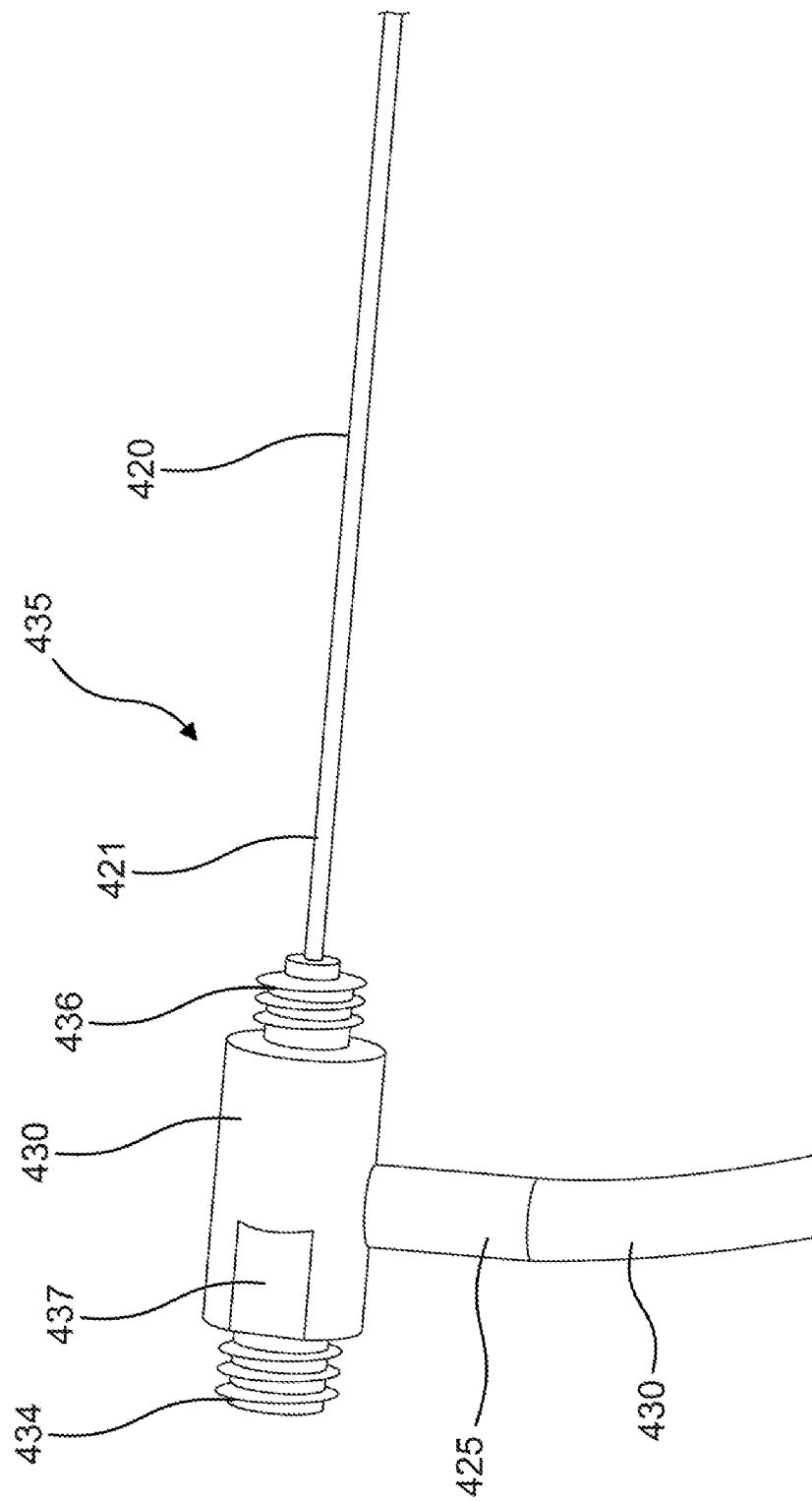
FIG. 19 is a side view of a proximal end portion of the inner probe of the probe assembly of FIG. 14.

FIGS. 9A-9C illustrate an example use of a probe assembly as described herein. FIG. 9A illustrates a schematic illustration of a probe assembly 210' including the first probe 235 and an alternative second (or outer) probe 245' disposed within a vessel V of a patient near or within an obstruction O. In this example illustration, the first probe 235 is disposed in a coaxial relationship with the second probe 245'. The second probe 245' can be configured the same as the second probe 245 or any of the second probes described herein. For example, the second probe 245 includes a second elongate member 244'. In this embodiment, the second elongate member 244' includes a tapered distal end portion 249'. In some embodiments, the tapered distal end portion 249' can be angled between 30 and 40 degrees relative to a centerline of the second elongate member 244'. As described above, the second probe 245' can be coupled to the first probe 235 in the same manner as described herein for other embodiments. As shown in FIG. 9A, a distal tip portion of the first probe 235 is extended outside of the second probe 245'. Although not shown, the distal portion of the probe assembly 210' can in some cases penetrate into the obstruction. With the distal portion of the probe assembly 210' inserted into the vessel V near or within the obstruction O (or penetrating the obstruction), the transducer assembly can be actuated to deliver ultrasonic energy along the first elongate member 220 of the first probe 235 and optionally the second elongate member 244' of the second probe 245' and into the obstruction. After delivering ultrasonic energy to at least partially disrupt the obstruction, in this example use, the first probe 235 is disconnected from the transducer assembly and from the second probe 245' and removed from the patient's body. The removal of the first probe 235 from within the second probe 245' can be performed while maintaining the second probe 245' within the vessel V. In some embodiments, the second probe 245' can be repositioned within the vessel V to at least partially penetrate into the obstruction (via the opening produced by the initial delivery of ultrasonic energy).

As shown in FIG. 9B, a third probe 275 includes a third elongate member 274 that is inserted through the lumen of the second probe 245'. The third probe 275 includes a third coupler (not shown) to couple the third probe 275 to the coupler (not shown) of the second probe 245'. As shown in FIG. 9B, the third elongate member 274 has a diameter greater than a diameter of the first elongate member 220 such that the third elongate member 274 cannot exit through the tapered distal end 249' of the second elongate member 244'. In other words, the third elongate member 274 has a distal tip that is sized to limit movement of the distal tip through the distal tip of the second elongate member 245'. With the third probe 275 disposed within the second probe 245', the distal portions of the second probe 245' and the third probe 275 can be positioned within the obstruction.

After inserting the third probe 275, the coupler of the second probe 245' can be coupled to the coupler of the third probe 275 by moving the second elongate member 244' proximally relative to the third elongate member 274, as shown by the arrow AA in FIG. 9B. The proximal movement of the second (outer) probe 245' causes the tapered distal tip portion 249' of the second elongate member 244' to engage a distal tip portion of the third elongate member 274. Continued proximal movement of the second (outer) probe 245' (to couple the second probe 245' to the coupler of the third probe 275), as shown by the arrow BB in FIG. 9C deforms a distal portion of the second elongate member 244' and/or a distal portion of the third elongate member 274 to produce a contact location C between the third elongate member 274 and the second elongate member 244'. Specifically, this deformation causes contact (or enhances the existing contact) between the outer surface of the third elongate member 274 and the inner surface of the second elongate member 244'. Ultrasonic energy can then be transmitted from the ultrasonic transducer assembly to at least the third probe 275, and at least a portion of the ultrasonic energy is delivered from the third elongate member 274 through the contact location C and the second elongate member 244' to the obstruction (as shown by ultrasonic energy US in FIG. 9C).

FIGS. 10A-13B illustrate another embodiment of an ultrasonic probe assembly that includes two ultrasonic probes and that can be coupled to and used within an ultrasonic energy ablation system, such as system 100 described above. In this embodiment, a probe assembly 310 includes a first probe 335 (see, e.g., FIGS. 12 and 13A), and a second probe 345 (see, e.g., FIGS. 12 and 13B) that can be releasably coupled to the first probe 335 as described in further details below. The first probe 335 includes a first elongate transmission member 320 (also referred to herein as "first transmission member" or "first elongate member" or "transmission member" or "elongate member") and a coupler 330. The coupler 330 includes a proximal end portion 331 and a distal end portion 332 and defines a central lumen 323 (see, e.g., FIG. 12) that extends at least partially the coupler 330. The coupler 330 also defines a side lumen 324 in fluid communication with the central lumen 323. In some embodiments, a side port (e.g., similar to the side port 425 described below) can be coupled to and/or within the side lumen 324 to provide aspiration and/or irrigation through the first probe 335. For example, the side lumen 324 can be coupled to and in fluid communication with a transfer line that can be used to supply irrigation or aspirate particles from an obstruction at the treatment site. An embodiment illustrating a fluid line is discussed below for probe assembly 410. In other embodiments, the coupler 330 need not include a side lumen, and can instead include only a central lumen therethrough that facilitates aspiration and/or irrigation. The proximal end portion 331 of the coupler 330 includes a first coupling portion 334 configured to be releasably coupled to a probe coupling (see e.g., the threaded probe coupling 168 in FIG. 2) at the distal end portion of the transducer assembly (e.g., distal end portion 165 of transducer assembly 150). For example, in this embodiment, the first coupling portion 334 is a threaded coupling that is threadably coupled within the transducer assembly 150 to a mating threaded probe coupling 168 within a lumen 166 at the distal end portion 165 of the transducer horn 163. In this manner, the first probe 335 can be removably coupled to the transducer assembly 150 via the coupler 330. The coupler 330 also includes two flat indented surfaces 337 that can be used to receive a tool to assist in securing the coupler 330 to the probe coupling. For example, a tool such as a medical wrench can clamp onto the surfaces 337 and used to tighten the coupler 230 to the probe coupling.

The distal end portion 332 of the coupler 330 is configured to receive a portion of the transmission member 320 to fixedly couple the transmission member 320 to the coupler 330 (i.e., within the central lumen 323). The transmission member 320 includes a proximal end portion 321 and a distal end portion 322. The proximal end portion 321 is fixedly coupled to the distal end portion 332 of the coupler 330. The distal end portion 322 is configured to be inserted into a body of a patient as described in more detail below. As described above, the first probe 335 also includes a second coupling portion 336 to releasably couple to the first probe 335 to the second probe 345.

The second probe 345 includes an elongate transmission member 344 (also referred to herein as "second transmission member" or "second elongate member" or "transmission member" or "elongate member") and a coupler 340. The coupler 340 includes a proximal end portion 343 and a distal end portion 347 and defines a lumen 339 (see, e.g., FIG. 12) that extends at least partially therethrough. The transmission member 344 includes a proximal end portion 341 and a distal end portion 342. The proximal end portion 341 is fixedly coupled to the distal end portion 347 of the coupler 340. The proximal end portion 343 of the coupler 340 includes a coupling portion 346 (also referred to herein as "third coupling portion") configured to be releasably coupled to the second coupling portion 336 of the first probe 335. Thus, the second probe 345 can be removably or releasably coupled to the transducer assembly 150 via the first probe 335 (e.g., via the coupler 330). In this manner, both the first probe 335 and the second probe 345 can be coupled to the same transducer assembly and be driven by the same ultrasonic transducer. More specifically, the lumen 348 of the second probe 345 can receive at least a portion of the first elongate member 320 of the first probe 335 and the coupler 340 can be releasably coupled to the coupler 330. The elongate member 320 of the first probe 335 can, for example, be inserted through the lumen 348 of the second elongate member 344 such that a distal end of the first elongate member 320 extends outside of the lumen 348. In this embodiment, the second coupling portion 336 is a threaded coupling and the third coupling portion 346 is a threaded coupling to threadably couple the first probe 335 to the second probe 346. The second probe 345 can also include a tapered distal end portion that can be incorporated into the second elongate member 344 or provided as a separate component. Such an embodiment is discussed below with reference to probe assembly 410, which includes a tapered distal end portion 449, or for the alternative second probe 245' (shown in FIGS. 9A-9C), which includes a tapered distal end portion 249'. The tapered distal end portion of the second probe 345 can assist with insertion of the probe assembly 310 into a tissue to be treated. In this manner, the second elongate member 344 can function as a guide catheter, as described below. By extending distally outside of the lumen 348, the distal end portion 322 of the elongate member 320 can be advanced into the target tissue.

The first elongate member 320 and the second elongate member 344 can each be any suitable shape, size, or configuration as described herein. In some embodiments, the elongate members 320 and 344 can optionally include any suitable feature configured to increase the flexibility (e.g., decrease the stiffness) of at least a portion of the transmission member 320, 344 thereby facilitating the passage of the elongate members 320, 344 through a tortuous lumen within a patient (e.g., a urinary tract, a vein, artery, etc.). For example, in some embodiments, a portion of the elongate members 320 and/or 344 can be formed from a material of lower stiffness than a different portion of the elongate member 320, 344 formed from a material of greater stiffness. In some embodiments, the stiffness of at least a portion of the elongate members 320 and/or 344 can be reduced by defining an opening (e.g., notch, a groove, a channel, a cutout, or the like), in the elongate members 320 and/or 344 or providing openings within a braided material in which the elongate members 320 and/or 344 may be formed, thereby reducing the area moment of inertia of the portion of the transmission members 320, 344.

Further, the first elongate member 320 can be formed with the same or different material than the second elongate member 344. In some embodiments, the second elongate member 344 is formed with a more flexible material than the first elongate member 320. In other words, first elongate member 320 has a stiffness greater than the second elongate member 344. In some embodiments, the second elongate member 344 is formed with a braided metal. The braided material can be the same as the braided material described above for elongate member 244.

As described above for previous embodiments, the first elongate member 320 can be disposed coaxial with the second elongate member 344 when the first elongate member 320 is disposed at least partially within the lumen 348 of the second elongate member 344. In other embodiments, the first elongate member 320 is non-coaxial with the second elongate member 344 when the first elongate member 320 is disposed at least partially within the lumen 348 of the second elongate member 344. In such a non-coaxial configuration, the close proximity or in some cases contact, between the first elongate member 320 and the second elongate member 344, allows for ultrasonic energy to be transferred from the first elongate member 320, to the second elongate member 344 and then to the target tissue, providing a greater amount of ultrasonic energy at the treatment site.

As described above for the previous embodiment, in use, a user (e.g., a surgeon, a technician, physician, etc.) can operate the ultrasonic system 100 (described above) to deliver ultrasonic energy to a target bodily tissue within a patient. For example, the ultrasonic system 100 and probe assembly 310 can be used to treat a chronic total occlusion (CTO) in a patient.

The probe assembly 310, having two ultrasonic probes (first probe 335 and second probe 345), allows the user to use both the first probe 335 and the second probe 345 to treat the target object, or the user can selectively decouple the second probe 345 from the first probe 335 such that ultrasonic energy is transferred only to the first elongate member 320. In such a use, the second probe 345 can function, for example, as a guide catheter. The user can also selectively couple and decouple the second probe 345 from the first probe 335 while the probe assembly 310 is inserted within the patient's body. For example, in some instances, a user can connect the first probe 335 to the transducer assembly and use the second probe 345 as a guide catheter for inserting the first probe 335 into the patient's body. Ultrasonic energy can be provided via the transducer of the transducer assembly to the first probe and to a target tissue to be treated. The user can then connect the second probe 345 to the first probe 335 (via the coupler 330 and the second coupler 340) thereby connecting the second probe 345 to the transducer assembly and transducer, and apply ultrasonic energy through both probes to the target tissue. In some instances, the second probe 345 may not be used. In some instances, both the first probe 335 and the second probe 345 are coupled to the transducer and ultrasonic energy is applied through both probes to the target tissue.

When at least the first probe 335 of the probe assembly 310 is coupled to the transducer assembly 150 (instead of the probe assembly 110), the first elongate member 320 can receive ultrasonic energy from the ultrasonic transducer (e.g., piezoelectric members 162) of the transducer assembly 150 and convey the ultrasonic energy to a target object within a patient's body. Similarly, when the second probe 345 is coupled to the first probe 335, the second elongate member 344 can receive ultrasonic energy from the ultrasonic transducer and convey the ultrasonic energy to the target object within the patient's body. Because the second (outer) probe 345 has a larger diameter, conveying the ultrasonic energy through the second probe 345 can produce a larger opening through the target tissue (e.g., CTO).

As described above, the user can, for example, engage the pedals 172 of the foot switch 170 such that the ultrasonic generator 180 generates an alternating current (AC) and voltage with a desired ultrasonic frequency (e.g., 20,000 Hz). In this manner, the ultrasonic generator 180 can supply AC electric power to the piezoelectric members 162. The AC electric power can urge the piezoelectric members 162 to oscillate (e.g., expand, contract, or otherwise deform) at the desired frequency, which, in turn, causes the transducer horn 163 to move relative to the housing 151. Thus, with the probe assembly 310 coupled to the transducer horn 163, the movement of the transducer horn 163 vibrates and/or moves the probe assembly 310, and more specifically, the first elongate member 320 and/or the second elongate member 344 when they are coupled to the transducer assembly 150.

In use, the distal end portion of the probe assembly 310 can be inserted within a vessel of a patient adjacent to or penetrating a target tissue (e.g., an obstruction, such as a CTO) such that the first elongate member 320 or the first elongate member 320 and the second elongate member 344 can transfer at least a portion of the ultrasonic energy to the target tissue. The distal end portion of the probe assembly 320 can be inserted into the vessel either before or after coupling the first probe 335 and/or second probe 345 to the transducer assembly. In some embodiments, a distal tip or end of the first elongate member 320 can extend outside of the lumen 348 of the second elongate member 344 and impact a target tissue such as, for example, to break apart an occlusion. In some embodiments, movement of the distal end portion 322 of the first elongate member 320 is such that cavitations occur within the portion of the patient. In this manner, the cavitation can further break apart a target tissue. As described herein, in some embodiments, the probe assembly 310 can optionally be used to aspirate and/or to supply irrigation to a target tissue site. For example, the port of the first probe can be coupled to a transfer line that can be used to supply irrigation or aspirate particles from an obstruction at the treatment site.

FIGS. 14-19 illustrate another embodiment of an ultrasonic probe assembly that includes two ultrasonic probes and that can be coupled to and used within an ultrasonic energy ablation system, such as system 100 described above. In this embodiment, a probe assembly 410 includes a first probe 435 (see, e.g., 15A), and a second probe 445 (see, e.g., FIGS. 15B) that can be releasably coupled to the first probe 435 as described in further detail below. The first probe 435 includes a first elongate transmission member 420 (also referred to herein as "first transmission member" or "first elongate member" or "transmission member" or "elongate member") and a coupler 430. The coupler 430 includes a proximal end portion 431 and a distal end portion 432 and defines a central lumen (not shown) that extends at least partially therethrough. The proximal end portion 431 of the coupler 430 includes a first coupling portion 434 configured to be releasably coupled to a probe coupling (see e.g., the threaded probe coupling 168 in FIG. 2) at the distal end portion of the transducer assembly (e.g., distal end portion 165 of transducer assembly 150). For example, in this embodiment, the first coupling portion 434 is a threaded coupling that is threadably coupled within the transducer assembly 150 to a mating threaded probe coupling 168 within a lumen 166 at the distal end portion 165 of the transducer horn 163. In this manner, the first probe 435 can be removably coupled to the transducer assembly 150 via the coupler 430. The coupler 430 also includes two flat indented surfaces 437 that can be used to receive a tool to assist in securing the coupler 430 to the probe coupling. For example, a tool such as a medical wrench can clamp onto the surfaces 437 and used to tighten the coupler 430 to the probe coupling.

The distal end portion 432 of the coupler 430 is configured to receive a portion of the transmission member 420 to fixedly couple the transmission member 420 to the coupler 430 (i.e., within the central lumen of the coupler 430). The transmission member 420 includes a proximal end portion 421 and a distal end portion 422. The proximal end portion 421 is fixedly coupled to the distal end portion 332 of the coupler 430. The distal end portion 422 is configured to be inserted into a body of a patient as described in more detail herein. As described above, the first probe 435 also includes a second coupling portion 436 to releasably couple to the first probe 435 to the second probe 445.

The second probe 445 includes an elongate transmission member 444 (also referred to herein as "second transmission member" or "second elongate member" or "transmission member" or "elongate member") and a coupler 440. The coupler 440 includes a proximal end portion 443 and a distal end portion 447 and defines a lumen 439 that extends at least partially therethrough. The transmission member 444 includes a proximal end portion 441 and a distal end portion 442. The proximal end portion 441 is fixedly coupled to the distal end portion 447 of the coupler 440. The proximal end portion 443 of the coupler 430 includes a coupling portion 446 (see, e.g., FIG. 18C) (also referred to herein as "third coupling portion") configured to be releasably coupled to the second coupling portion 436 of the first probe 435. Thus, the second probe 445 can be removably or releasably coupled to the transducer assembly 150 via the first probe 435 (e.g., via the coupler 430). In this manner, both the first probe 435 and the second probe 445 can be coupled to the same transducer assembly and be driven by the same ultrasonic transducer. More specifically, the lumen of the second probe 445 can receive at least a portion of the first elongate member 420 of the first probe 435 and the coupler 440 can be releasably coupled to the coupler 430. The elongate member 420 of the first probe 435 can, for example, be inserted through the lumen of the second elongate member 444 such that a distal end of the first elongate member 420 extends outside of the lumen 448 as shown, for example, in FIGS. 14 and 17B. In this embodiment, the second coupling portion 436 is a threaded coupling and the third coupling portion 446 is a threaded coupling (see, e.g., FIG. 18C) to threadably couple the first probe 435 to the second probe 446. The second probe 445 can also include a tapered distal end portion 449 that is in this embodiment a separate component coupled to the distal end portion 442 of the second elongate member 444. The tapered distal end portion 449 of the second probe 445 can assist with insertion of the probe assembly 410 into a tissue to be treated. In this manner, the second elongate member 444 can function as a guide catheter, as described below. By extending distally outside of the lumen 448, the distal end portion 422 of the elongate member 420 can be advanced into the target tissue. In some embodiments, the tapered distal end portion 449 can provide an angled distal end that is angled between 30 and 40 degrees relative to a centerline of the second elongate member 444.

The first coupler 430 also includes a port 425 in fluid communication with the central lumen of the first elongate member 420. The port 425 can be used to aspirate and/or to supply irrigation to a target tissue site. The port 425 is coupled to a transfer line 426 that can be coupled to a fluid source or disposal container via a connector 427 (see, e.g., FIGS. 14 and 15A). The port 425 and fluid line 426 can be used to supply irrigation or aspirate particles from an obstruction at the treatment site.

The first elongate member 420 and the second elongate member 444 can each be any suitable shape, size, or configuration as described herein. In this embodiment, the first elongate member 420 is formed with a metal such as stainless steel, and the second elongate member 444 is formed with a braided metal material. The braided metal of the second elongate member 444 is more flexible than the stainless steel of the first elongate member 420. Thus, the first elongate member 420 has a stiffness greater than the second elongate member 444. In alternative embodiments, the first elongate member 420 can be formed with the same material than the second elongate member 444. The combination of a flexible braided second elongate member 444 and a more rigid inner elongate member 420 provides both strength in the probe assembly 410 and flexibility to maneuver the probe assembly 410 through a vessel of a patient.

In some embodiments, the elongate members 420 and 444 can optionally include any suitable feature configured to increase the flexibility (e.g., decrease the stiffness) of at least a portion of the transmission member 420, 444 thereby facilitating the passage of the elongate members 420, 444 through a tortuous lumen within a patient (e.g., a urinary tract, a vein, artery, etc.). For example, in some embodiments, a portion of the elongate members 420 and/or 444 can be formed from a material of lower stiffness than a different portion of the elongate member 420, 444 formed from a material of greater stiffness. In some embodiments, the stiffness of at least a portion of the elongate members 420 and/or 444 can be reduced by defining an opening (e.g., notch, a groove, a channel, a cutout, or the like), in the elongate members 420 and/or 444 or providing openings within a braided material in which the elongate members 420 and/or 444 may be formed, thereby reducing the area moment of inertia of the portion of the transmission members 420, 444.

As described above for previous embodiments, the first elongate member 420 can be disposed coaxial with the second elongate member 444 when the first elongate member 420 is disposed at least partially within the lumen of the second elongate member 344. In other embodiments, the first elongate member 420 is non-coaxial with the second elongate member 444 when the first elongate member 420 is disposed at least partially within the lumen 448 of the second elongate member 444. In such a non-coaxial configuration, the close proximity or in some cases contact, between the first elongate member 420 and the second elongate member 444, allows for ultrasonic energy to be transferred from the first elongate member 420, to the second elongate member 444 and then to the target tissue, providing a greater amount of ultrasonic energy at the treatment site.

As also described above for the previous embodiment, in use, a user (e.g., a surgeon, a technician, physician, etc.) can operate the ultrasonic system 100 (described above) to deliver ultrasonic energy to a target bodily tissue within a patient. For example, the ultrasonic system 100 and probe assembly 410 can be used to treat a chronic total occlusion (CTO) in a patient.

The probe assembly 410, having two ultrasonic probes (first probe 435 and second probe 445), allows the user to use both the first probe 435 and the second probe 445 to treat the target object, or the user can selectively decouple the second probe 445 from the first probe 435 such that ultrasonic energy is transferred only to the first elongate member 420. In such a use, the second probe 445 can function, for example, as a guide catheter. The user can also selectively couple and decouple the second probe 445 from the first probe 435 while the probe assembly 410 is inserted within the patient's body. For example, in some instances, a user can connect the first probe 435 to the transducer assembly and use the second probe 445 as a guide catheter for inserting the first probe 435 into the patient's body. Ultrasonic energy can be provided via the transducer of the transducer assembly to the first probe and to a target tissue to be treated. The user can then connect the second probe 445 to the first probe 435 (via the coupler 430 and the second coupler 440) thereby connecting the second probe 245 to the transducer assembly and transducer, and apply ultrasonic energy through both probes to the target tissue. In some instances, the second probe 445 may not be used. In some instances, both the first probe 435 and the second probe 445 are coupled to the transducer and ultrasonic energy is applied through both probes to the target tissue.

When at least the first probe 435 of the probe assembly 410 is coupled to the transducer assembly 150 (instead of the probe assembly 110), the first elongate member 420 can receive ultrasonic energy from the ultrasonic transducer (e.g., piezoelectric members 162) of the transducer assembly 150 and convey the ultrasonic energy to a target object within a patient's body. Similarly, when the second probe 445 is coupled to the first probe 435, the second elongate member 444 can receive ultrasonic energy from the ultrasonic transducer and convey the ultrasonic energy to the target object within the patient's body. Because the second (outer) probe 445 has a larger diameter, conveying the ultrasonic energy through the second probe 445 can produce a larger opening through the target tissue (e.g., CTO).

As described above, the user can, for example, engage the pedals 172 of the foot switch 170 such that the ultrasonic generator 180 generates an alternating current (AC) and voltage with a desired ultrasonic frequency (e.g., 20,000 Hz). In this manner, the ultrasonic generator 180 can supply AC electric power to the piezoelectric members 162. The AC electric power can urge the piezoelectric members 162 to oscillate (e.g., expand, contract, or otherwise deform) at the desired frequency, which, in turn, causes the transducer horn 163 to move relative to the housing 151. Thus, with the probe assembly 410 coupled to the transducer horn 163, the movement of the transducer horn 163 vibrates and/or moves the probe assembly 410, and more specifically, the first elongate member 420 and/or the second elongate member 444 when they are coupled to the transducer assembly 150.

In use, the distal end portion of the probe assembly 410 can be inserted within a vessel of a patient adjacent to or penetrating a target tissue (e.g., an obstruction, such as a CTO) such that the first elongate member 420 or the first elongate member 420 and the second elongate member 444 can transfer at least a portion of the ultrasonic energy to the target tissue. The distal end portion of the probe assembly 420 can be inserted into the vessel either before or after coupling the first probe 435 and/or second probe 445 to the transducer assembly. In some embodiments, a distal tip or end of the first elongate member 420 can extend outside of the lumen of the second elongate member 444 and impact a target tissue such as, for example, to break apart an occlusion. In some embodiments, movement of the distal end portion 422 of the first elongate member 420 is such that cavitations occur within the portion of the patient. In this manner, the cavitation can further break apart a target tissue.

Figure 20:
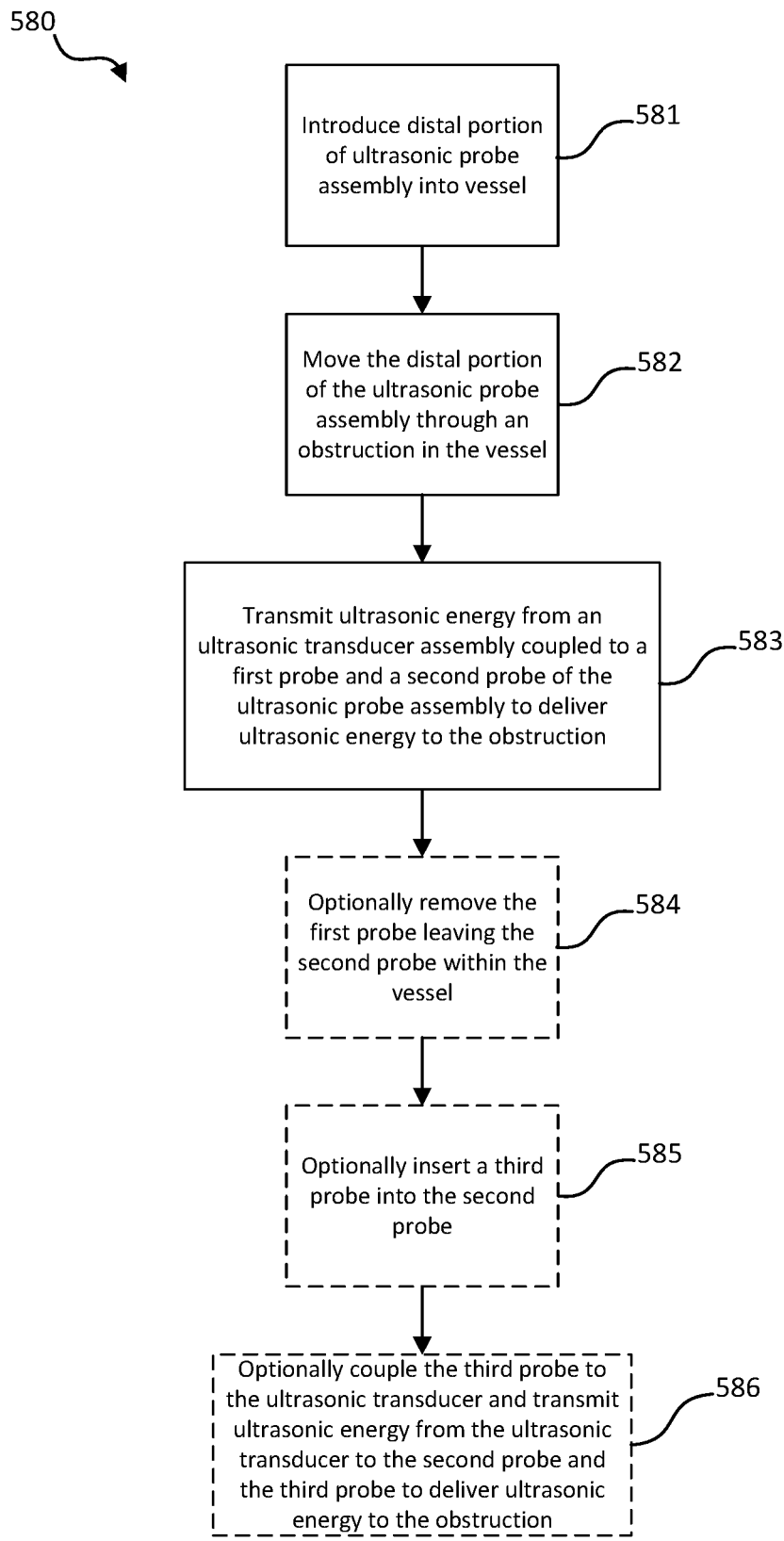
FIG. 20 is a flowchart illustrating a method for transferring ultrasonic energy to a bodily tissue.

FIG. 20 is a flowchart illustrating a method 580 for transferring ultrasonic energy to a target tissue within a body of a patient using an ultrasonic probe assembly as described herein, according to an embodiment. In some embodiments, the method 580 includes inserting or introducing at least a distal end portion of a probe assembly (e.g., probe assembly 210, 310, 410) into a vessel of a patient, at 581. The probe assembly can include a first probe and a second probe each couplable to an ultrasonic transducer assembly (e.g., 150) of an ultrasonic ablation system (e.g., 100). The first probe includes a first coupler and a first elongate member coupled to the first coupler, and is couplable o the transducer assembly via the first coupler. The second probe includes a second coupler and a second elongate member coupled to the second coupler, and the second coupler is releasably coupled to the first coupler such that the second probe is coupled to the ultrasonic transducer assembly via the first probe. In some embodiments, prior to introducing the distal portion of the probe assembly into the vessel, the second probe is coupled to the first probe by inserting the first elongate member of the first probe through a lumen of the second probe such that a distal tip portion of the first elongate member extends outside the lumen of the second elongate member.

At 582, the distal portion of the ultrasonic probe assembly is moved through an obstruction in the vessel such that a distal end portion of the first elongate member penetrates the obstruction and a distal end portion of the second elongate member penetrates the obstruction. At 583, ultrasonic energy is transmitted from the ultrasonic transducer assembly to the first probe and to the second probe such that ultrasonic energy is delivered through the first elongate member and the second elongate member to the obstruction.

In some embodiments, after transmitting ultrasonic energy to the first probe and the second probe, the distal end portion of the ultrasonic probe assembly is moved within the obstruction from a first location to a second location within the obstruction and ultrasonic energy is transmitted to the first probe and to the second probe such that ultrasonic energy is delivered through the first elongate member and the second elongate member to the second location within the obstruction and disrupts at least a portion of the obstruction.

In some embodiments, at 584, after transmitting the ultrasonic energy, the second probe is optionally disconnected from the first probe and from the ultrasonic transducer assembly, and the first probe is removed from the vessel leaving the second probe disposed within the vessel. At 585, a third ultrasonic probe is inserted into the lumen of the second probe. In some embodiments, the third probe has a third coupler and a third elongate member coupled to the third coupler. In some embodiments, the third elongate member has a distal end portion having a diameter greater than a diameter of a distal end portion of the first elongate member such that at least a portion of the distal end portion of the third elongate member contacts an inside wall of the second elongate member at a contact location on the second elongate member.

At 586, the third probe is coupled to the ultrasonic transducer assembly and ultrasonic energy is transmitted to the third probe and to the second probe such that ultrasonic energy is delivered through the third elongate member and the second elongate member to the obstruction. In some embodiments, during the transmitting ultrasonic energy to the third probe, ultrasonic energy is delivered from the portion of the distal end portion of the third elongate member to the second elongate member where the portion of the distal end portion of the third elongate member contacts the inside wall of the second elongate member at the contact location such that ultrasonic energy is delivered to the obstruction proximate to the contact location.

The embodiments and/or components described herein can be packaged independently or any portion of the embodiments can be packaged together as a kit. For example, in some embodiments, a kit can include an ultrasonic transducer assembly (e.g., such as the ultrasonic transducer assembly 150 described above with reference to FIG. 2) and a probe assembly (e.g., 210, 310, 410), as described herein.

The processor included in any of the ultrasonic generators can be a general-purpose processor (e.g., a central processing unit (CPU)) or other processor configured to execute one or more instructions stored in the memory. In some embodiments, the processor can alternatively be an application-specific integrated circuit (ASIC) or a field programmable gate array (FPGA). The processor can be configured to execute specific modules and/or sub-modules that can be, for example, hardware modules, software modules stored in the memory and executed in the processor, and/or any combination thereof. The memory included in the ultrasonic generator 180 can be, for example, flash memory, one time programmable memory, a random access memory (RAM), a memory buffer, a hard drive, a read-only memory (ROM), an erasable programmable read-only memory (EPROM), and/or so forth. In some embodiments, the memory includes a set of instructions to cause the processor to execute modules, processes and/or functions used to generate, control, amplify, and/or transfer electric current to another portion of the system, for example, the transducer assembly 150.

Some embodiments described herein, such as, for example, embodiments related to the ultrasonic generators described above, relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. Additionally certain events may be performed concurrently in parallel processes when possible, as well as performed sequentially. While the embodiments have been particularly shown and described, it will be understood that various changes in form and details may be made. Although various embodiments have been described as having particular features and/or combinations of components, other embodiments are possible having a combination of any features and/or components from any of embodiments where appropriate.

For example, the probe assemblies described above (110, 210, 310, 410) can be used in any suitable ultrasonic energy system, such as the ultrasonic energy system 100 described with reference to FIGS. 1 and 2. As described above, the first and second probes of the probe assemblies can be coupled and decoupled from each other to allow a user to selectively use only the first probe or both the first probe and the second probe of the probe assembly to treat a target object. The elongate transmission members of the probe assemblies described herein can have various shapes and sizes (e.g., diameters, lengths, etc.). For example, in some embodiments, an outer elongate transmission member can have an outer diameter that is between 0.95 mm and 2.5 mm, and an inner diameter that is between 0.5 mm and 2.3 mm, and an inner elongate transmission member can have an outer diameter that is between 0.4 mm and 2.2 mm and an inner diameter that is between 0.1 mm and 2.0 mm. In some embodiments, an outer elongate transmission member can have a length that is between 450 mm and 1790 mm, and an inner elongate transmission member can have a length that is between 460 mm and 1800 mm.

Although the transducer assembly 150 is shown in FIG. 2 as including two insulators 161 and two piezoelectric rings 162, in other embodiments, a transducer assembly can include any suitable number of insulators 161 and/or piezoelectric rings 162 in any suitable arrangement. Moreover, the insulators 161 can be formed from any suitable insulating material, ceramic materials (e.g., polyamide, expanded polytetraflouroethylene (EPTFE), or the like). Similarly, the piezoelectric rings 162 can be any suitable piezoelectric material (e.g., lead zirkonate titanate (PZT-5), PZT-8, lead titanate (PT), lead metaniobate ($PbNbO_6$), polyvinylidenefluoride (PVDF), or the like).

What is claimed is:

1. An apparatus, comprising:
    a transducer assembly including a transducer housing and an ultrasonic transducer disposed within the transducer housing;
    a transducer horn disposed at least partially within the transducer housing and including a probe coupling;
    a first probe including a first coupler and a first elongate member coupled to the first coupler, the first coupler having a first coupling portion and a second coupling portion, the first coupling portion configured to be releasably coupled directly to the probe coupling of the transducer horn such that the first probe is coupled to the ultrasonic transducer; and
    a second probe including a second coupler and a second elongate member coupled to the second coupler, the second coupler having a third coupling portion releasably couplable directly to the second coupling portion of the first coupler such that the second probe is coupled to the ultrasonic transducer,
    each of the first elongate member and the second elongate member are configured to receive ultrasonic energy from the ultrasonic transducer and convey the ultrasonic energy to a target object within a patient's body when the second probe is coupled to the first probe.

2. The apparatus of claim 1, wherein the first coupling portion is a threaded coupling, the probe coupling is a threaded coupling such that the first probe is threadably couplable to the transducer horn.

3. The apparatus of claim 1, wherein the second coupling portion of the first probe is a threaded coupling and the third coupling portion of the second coupler is a threaded coupling such that the second probe is threadably couplable to the first coupler.

4. The apparatus of claim 1, wherein the second elongate member of the second probe includes a proximal end and a distal end and defines a lumen between the proximal end and the distal end, the first elongate member of the first probe configured to be disposed at least partially within the lumen of the second elongate member.

5. The apparatus of claim 4, wherein the first elongate member is coaxial with the second elongate member when the first elongate member is disposed at least partially within the lumen of the second elongate member.

6. The apparatus of claim 1, wherein the first elongate member is formed with a first material, and the second elongate member is formed with a second material different from the first material.

7. The apparatus of claim 6, wherein the second material is a braided metal.

8. The apparatus of claim 1, wherein the first elongate member has a stiffness greater than the second elongate member.

9. The apparatus of claim 1, wherein the second elongate member is more flexible than the first elongate member.

10. The apparatus of claim 1, wherein:
    the first elongate member has a proximal end and a distal end and defines a lumen extending between the proximal end and the distal end;
    the first coupler defines a port in fluid communication with the lumen of the first elongate member, the apparatus, further comprising:
    a transfer line coupled to the first probe and in fluid communication with the port.

* * * * *